US010869472B2

(12) United States Patent
Katou et al.

(10) Patent No.: US 10,869,472 B2
(45) Date of Patent: Dec. 22, 2020

(54) SET FOR CULTURE VESSEL TRANSPORT AND CELL/BIOLOGICAL TISSUE TRANSPORT UNIT

(71) Applicant: SANPLATEC CORPORATION LTD., Osaka (JP)

(72) Inventors: Satoshi Katou, Osaka (JP); Junichi Kuwabara, Osaka (JP); Yuki Iwamoto, Osaka (JP); Hidenori Nakajima, Kyoto (JP); Yoshifumi Kobayashi, Kyoto (JP)

(73) Assignee: SANPLATEC CORPORATION LTD., Osaka (JP)

( * ) Notice: Subject to any disclaimer, the term of this patent is extended or adjusted under 35 U.S.C. 154(b) by 103 days.

(21) Appl. No.: 15/739,604

(22) PCT Filed: Jun. 24, 2015

(86) PCT No.: PCT/JP2015/068271
§ 371 (c)(1),
(2) Date: Dec. 22, 2017

(87) PCT Pub. No.: WO2016/208018
PCT Pub. Date: Dec. 29, 2016

(65) Prior Publication Data
US 2018/0177181 A1    Jun. 28, 2018

(51) Int. Cl.
*C12M 1/00* (2006.01)
*C12M 3/00* (2006.01)
*A01N 1/02* (2006.01)
*A61J 1/14* (2006.01)
*A61J 1/20* (2006.01)
*C12M 1/34* (2006.01)
*C12M 1/22* (2006.01)

(52) U.S. Cl.
CPC ......... *A01N 1/0273* (2013.01); *A01N 1/0242* (2013.01); *A61J 1/1406* (2013.01);
(Continued)

(58) Field of Classification Search
CPC ... A01N 1/0273; C12M 23/38; B01L 2200/18
(Continued)

(56) References Cited

U.S. PATENT DOCUMENTS 5,766,936 A * 6/1998 Kayal ................ C12M 23/08
215/354
2004/0005699 A1* 1/2004 Roos ................. C12M 23/12
435/297.5
(Continued)

FOREIGN PATENT DOCUMENTS

JP    2002-159284 A    6/2002
JP    2009-089715 A    4/2009
(Continued)

OTHER PUBLICATIONS

International Search Report and Written Opinion, International Patent Application No. PCT/JP2015/068271, dated Sep. 15, 2015, with English translation of Search Report (10 pages).

*Primary Examiner* — Holly Kipouros
(74) *Attorney, Agent, or Firm* — Hamre, Schumann, Mueller & Larson, P.C.

(57) ABSTRACT

A culture container transporting set A1 includes: a culture container 1 having a vessel 13 made of a bottom wall 11 and a tubular side wall 12 raised from the bottom wall 11; a flexible cover 2 that covers an upper end 121 of the side wall 12; a presser member 3 that is relatively hard and placed on the cover 2; and a holder 5 that holds the culture container 1, the cover 2 and the presser member 3 integral as stacked into an assembled state, by applying pressure from top and bottom.

12 Claims, 21 Drawing Sheets

(52) U.S. Cl.
 CPC ............ *A61J 1/2096* (2013.01); *C12M 23/38* (2013.01); *C12M 23/48* (2013.01); *C12M 23/52* (2013.01); *C12M 41/32* (2013.01); *C12M 45/22* (2013.01)

(58) Field of Classification Search
 USPC ...................................................... 435/307.1
 See application file for complete search history.

(56) References Cited

U.S. PATENT DOCUMENTS

| | | | |
|---|---|---|---|
| 2007/0212750 A1* | 9/2007 | Kieffer | C12M 23/26 435/34 |
| 2010/0062528 A1 | 3/2010 | Chesne et al. | |
| 2010/0079751 A1* | 4/2010 | Porat | B01L 3/502 356/300 |
| 2013/0344579 A1* | 12/2013 | Izapy | B01L 3/508 435/288.3 |
| 2014/0302602 A1 | 10/2014 | Kawasaki | |
| 2015/0075301 A1* | 3/2015 | Scialo | G01N 1/2208 73/863.22 |
| 2015/0231628 A1 | 8/2015 | Nozaki et al. | |

FOREIGN PATENT DOCUMENTS

| | | |
|---|---|---|
| JP | 2010-503390 A | 2/2010 |
| JP | 2013-039103 A | 2/2013 |
| JP | 2013-128457 A | 7/2013 |
| WO | 2013/094370 A1 | 6/2013 |
| WO | 2014/041593 A1 | 3/2014 |

\* cited by examiner

SET FOR CULTURE VESSEL TRANSPORT AND CELL/BIOLOGICAL TISSUE TRANSPORT UNIT

TECHNICAL FIELD

The present invention relates to a technology for transporting living cells and tissues maintained in a cultured stated. The present invention specifically relates to a technology of transportation using a culture container that is commonly used in the research fields.

BACKGROUND ART

Culture containers are widely used for cultivation of living cells and tissues and examples include petri dishes (receivers), well plates and probes. Such culture containers are designed for cultivation in ventilated conditions. Although a lid may be provided, the lid is simply placed on the container without hermetic sealing. A typical way to seal a culture container is to attach an adhesive film to the upper end of the tubular wall of the container. Another scheme proposed is to use an elastomer sheet to cover the upper end of the tubular wall of the container (see Patent Document 1).

In cell culture, cells will proliferate while they are covered with a necessary amount of culture medium in a culture container. Conventionally, it is common to transport cultured cells refrigerated, which requires the following. Before the refrigerated transportation, the cultured cells need to be transferred from a culture container to a special container for cryopreservation and then refrigerated. After the transportation, the cells need to be thawed and transferred to a culture container in which a necessary amount of culture medium has been injected. Unfortunately, transferring cells between containers involves the risk of contamination and cell loss. In addition, a significant amount of time and technical challenges are required for freezing/thawing to make the cell usable. Recent advances in constant-temperature transportation technology have made it possible to transport non-refrigerated cells at the temperatures suitable for culture. Cultured cells transported in the cultured state are ready to be used for experiments, researches, etc. at the destination.

A culture container to be transported may be dully sealed using an adhesive film described above. However, the culture medium is expected to directly contact the adhesive surface of the film, causing a risk of contamination by eluded adhesive. In addition, when the adhesive film is peeled off, the contents may be spilled from the container due to vibration. The scheme of using an elastomer sheet to cover a container fails to provide a sufficiently reliable liquid seal during transportation.

PRIOR ART DOCUMENT

Patent Document

Patent Document 1: JP-A-2002-159284

SUMMARY OF THE INVENTION

Problems to be Solved by the Invention

The present invention has been devised under the above-noted problems, and aims to provide a culture container transporting set suitable for transportation in a manner to maintain a cultured state.

Means to Solve the Problems

To solve the problems noted above, the present invention employs the following technical solutions.

A first aspect of the present invention provides a culture container transporting set including: a culture container having at least one vessel including a bottom wall and a tubular side wall raised from the bottom wall; a flexible cover that covers an upper end of the side wall of the vessel; a presser member that is relatively hard and placed on the cover; and a holder that holds the culture container, the cover and the presser member integral in an assembled state in which the culture container, the cover and the presser member are stacked, by applying pressure from top and bottom.

In a preferred embodiment, the cover includes: a thick portion having a relatively large thickness and in intimate contact with the upper end of the side wall; and a thin portion having a relatively small thickness and surrounded by the thick portion as viewed in a vertical direction.

In a preferred embodiment, the thick portion has a re-sealing ability to seal a syringe needle puncture. In the assembled state, the thick portion is in intimate contact with a lower surface of the presser member.

In a preferred embodiment, the cover has a projected portion accommodated inside the side wall to project toward the bottom wall.

In a preferred embodiment, the cover is formed of a film having gas permeability.

In a preferred embodiment, wherein the cover is formed of a film without gas permeability.

In a preferred embodiment, the presser member includes a tubular portion accommodated inside the side wall to extend downward toward the bottom wall.

In a preferred embodiment, the presser member is provided with a through-hole extending vertically at a location inside the side wall as viewed in the vertical direction.

In a preferred embodiment, the presser member is provided with a groove formed in an upper surface of the presser member to connect a peripheral edge of the presser member to the through-hole.

In a preferred embodiment, the holder includes a flat bottom plate, a top plate parallel to the bottom plate, and a pair of side plates each connected at opposite ends to the top plate and the top plate. The plates are connected to define a closed outline.

In a preferred embodiment, the holder includes: a bottom member having a flat bottom plate; a lid member detachably attached to the bottom member and having a top plate parallel to the bottom plate; and a fastening means for fastening the bottom member and the lid member.

In a preferred embodiment, there is additionally provided an elastic sheet member having an ability to return to an original shape. In the assembled state, the elastic sheet member is stacked in contact with one of the culture container, the cover and the presser member.

In a preferred embodiment, there is additionally provided a side-surface cover that covers an entirety of a side surface of the bottom wall and a part of a side surface of the elastic sheet member.

A second aspect of the present invention provides a living cell and tissue transporting unit including: the culture container transporting set according to the first aspect of the present invention; and a living cell or tissue and a culture medium that are stored in the vessel of the culture container transporting set.

MODE FOR CARRYING OUT THE INVENTION

Preferred embodiments of the present invention are specifically described below with reference to the drawings.

Figure 1:
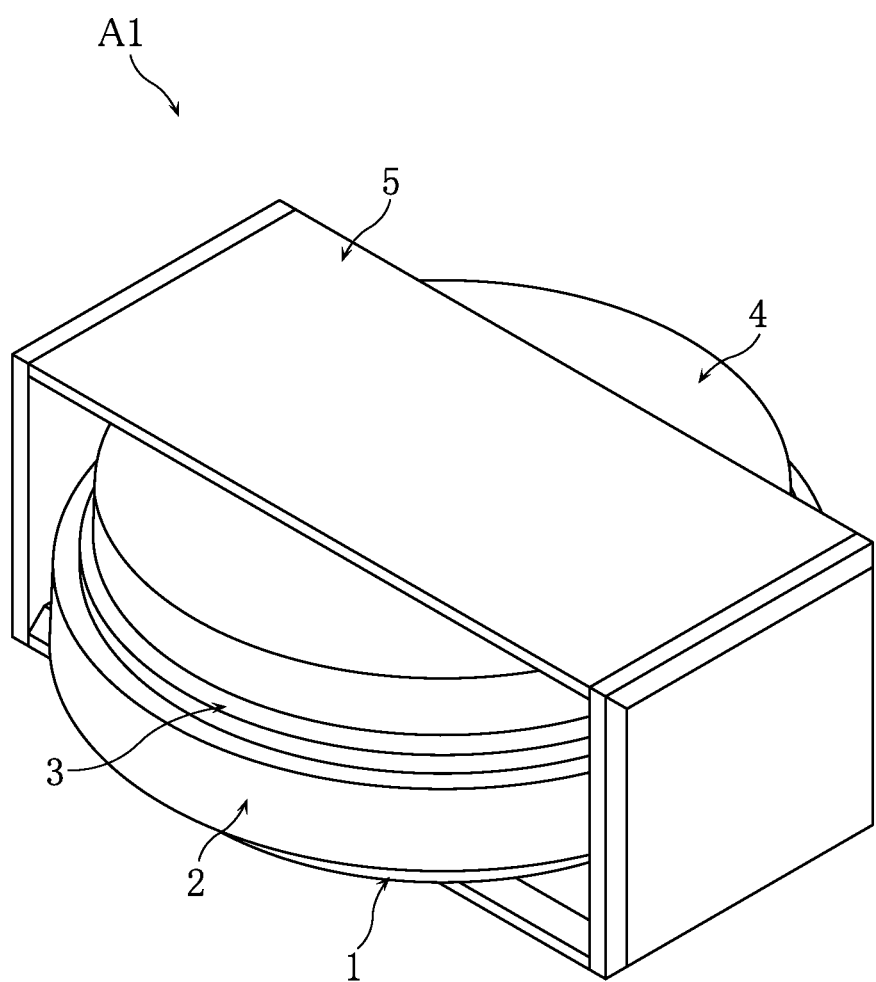
FIG. 1 is a perspective view showing a first embodiment of a culture container transporting set according to the present invention.
Figure 2:
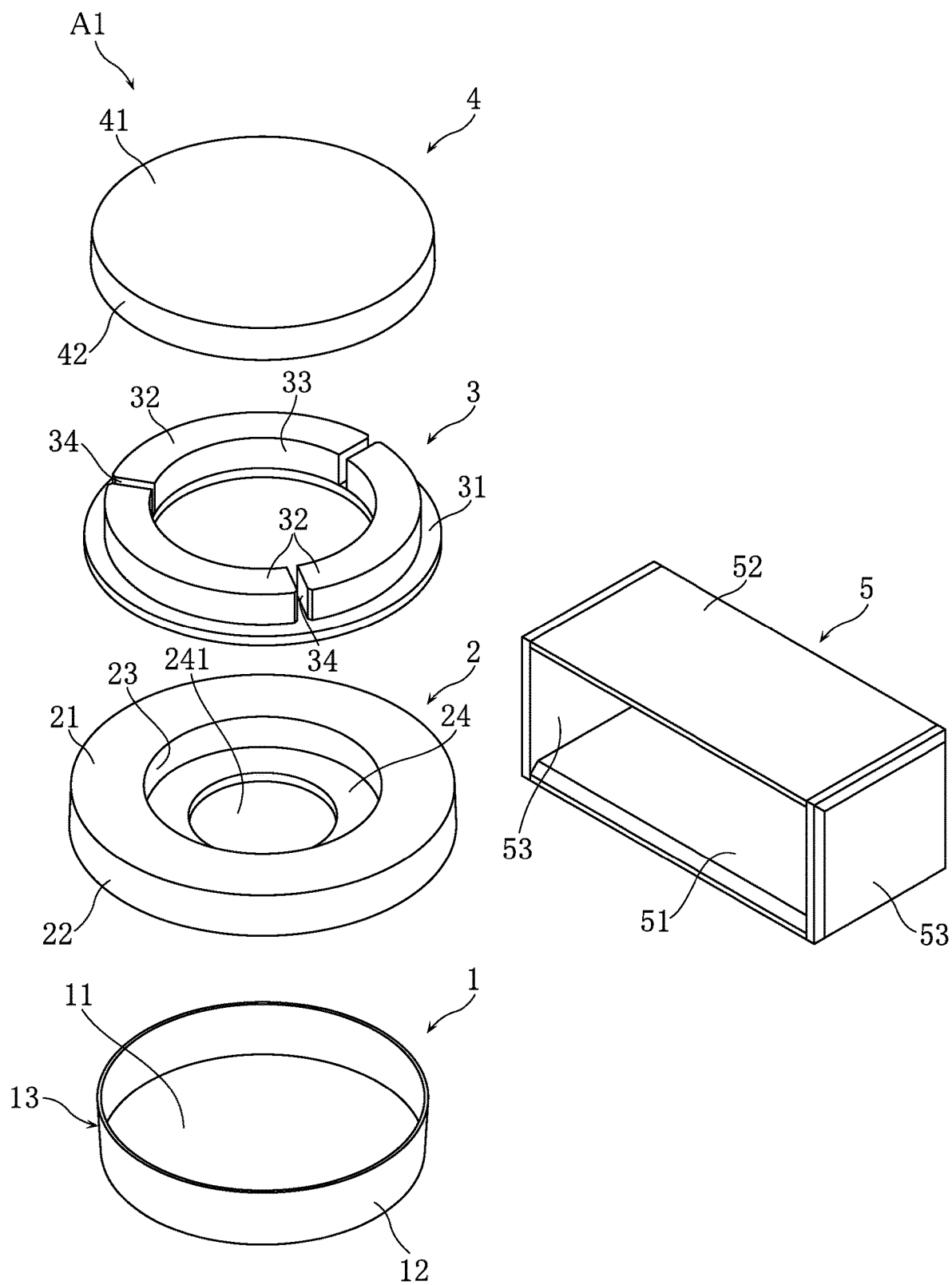
FIG. 2 is an exploded perspective view of the culture container transporting set shown in FIG. 1.
Figure 3:
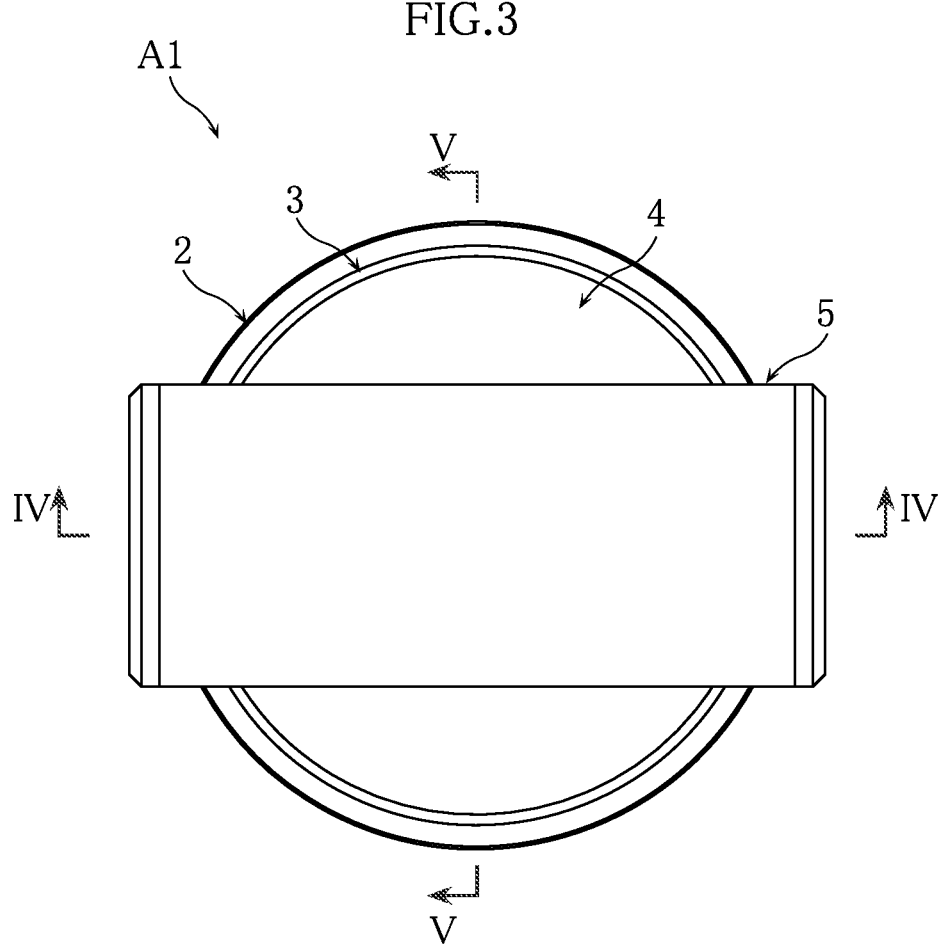
FIG. 3 is a plan view of the culture container transporting set shown in FIG. 1.

FIGS. 1 to 5 show a first embodiment of a culture container transporting set according to the present invention. The culture container transporting set A1 of the present embodiment includes a culture container 1, a cover 2, a presser member 3, a lid 4 and a holder 5. FIGS. 1 and 3 to 5 show an assembled state in which the culture container 1, the cover 2, the presser member 3 and the lid 4 are stacked. FIG. 2 is a perspective view showing the parts of the culture container transporting set A1 in a disassembled state.

In the present embodiment, the culture container 1 corresponds to a petri dish (receiver) and includes a vessel 13 constituted of a bottom wall 11 and a tubular side wall 12 raised from the peripheral edge of the bottom wall 11. The vessel 13 (the culture container 1) is for storing cultured cells and a culture medium therein. The culture container 1 is formed of a transparent plastic material, for example. Examples of such a transparent plastic material include polystyrene and methyl pentene, which are commonly used as medical grade plastics, as well as other materials, such as cycloolefin polymers and cycloolefin copolymers. Although these transparent materials are preferable, other materials may be used. For the vessel 13 to be suitable for cultivation of adherent cells, the culture surface to which the cells adhere (the upper surface of the bottom wall 11) may be subjected to a treatment for providing hydrophilicity by, for example, corona discharge or plasma discharge.

The cover 2 is placed on the vessel 13 from above to close the opening of the vessel 13. The cover 2 is formed of a flexible and resilient material. Preferably, in addition, the cover 2 is self-adhesive. The cover 2 may be formed of silicone rubber, natural rubber, urethane rubber or elastomer resin, among which silicone rubber is preferable. In view of potential contact between the cover 2 and the contents of the culture container 1 (cultured cells and culture medium), the cover 2 is more preferably formed of a medical grade silicone rubber, which is without cytotoxicity and has biocompatibility. With respect to the hardness, the cover 2 preferably has a rubber hardness of 20 to 40 degrees or so.

Figure 4:
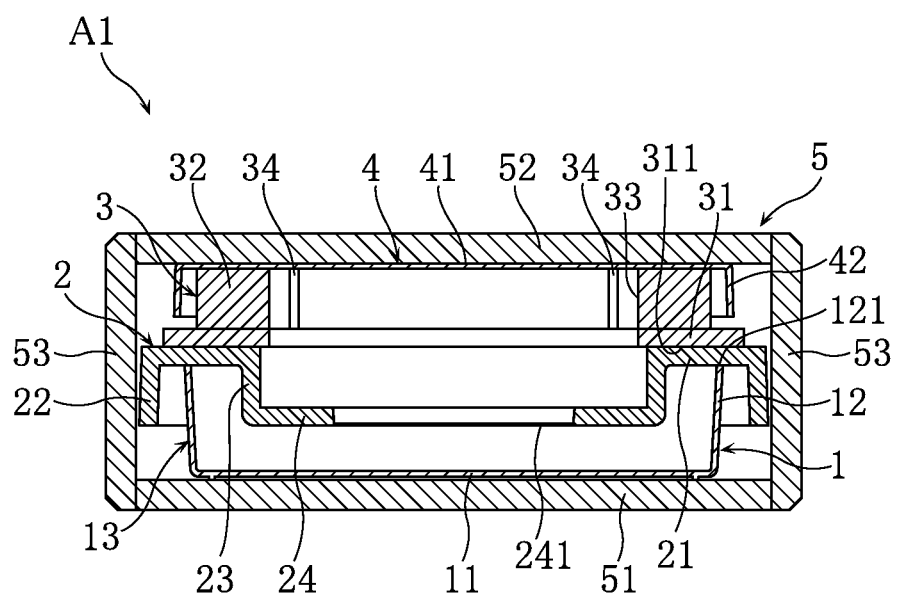
FIG. 4 is a sectional view taken along line IV-IV of FIG. 3.
Figure 5:
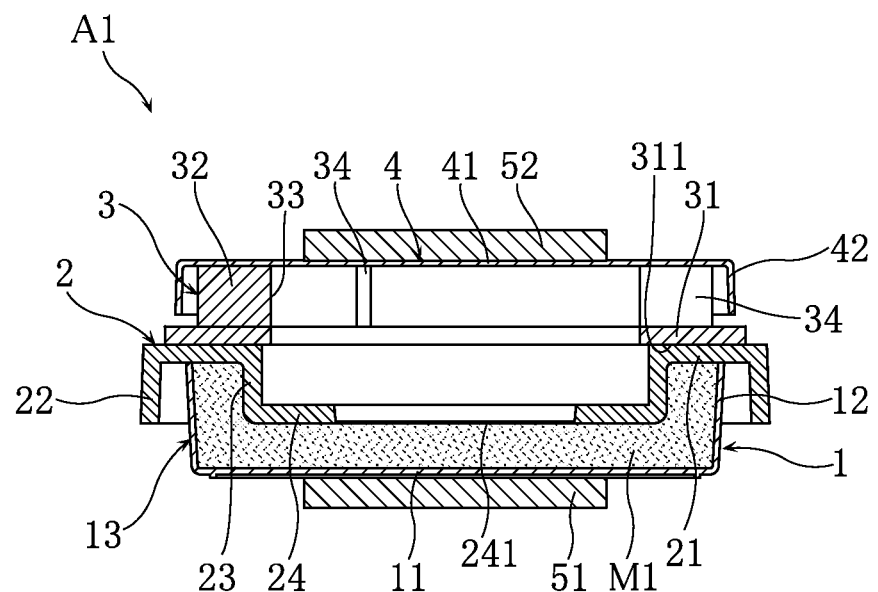
FIG. 5 is a sectional view taken along line V-V of FIG. 3, with contents stored in a vessel.

The cover 2 may be a rubber molded product and includes, as shown in FIGS. 2, 4 and 5, a planar annular portion 21, an outer cylindrical portion 22 extending downward from the outer peripheral edge of the annular portion 21, an inner cylindrical portion 23 extending downward from the inner peripheral edge of the annular portion 21, and a bottom 24 closing the lower end of the inner cylindrical portion 23.

The annular portion 21 is in intimate contact with an upper end 121 of the side wall 12 and extends over the side wall 12 to cover a location radially outside and a location radially inside the side wall. The annular portion 21 has an appropriate thickness and appropriate elastic resilience against the load applied in a vertical direction. In one example, the thickness of the annular portion 21 may be 1 to 3 mm or so. The annular portion 21 corresponds to the thick portion of the present invention. As a result that the annular portion 21 has an appropriate thickness and elastic resilience, the annular portion 21 achieves a re-sealing ability to seal syringe needle punctures.

As shown in FIGS. 4 and 5, the inner cylindrical portion 23 and the bottom 24 are accommodated inside the side wall 12 of the vessel 13 and vertically extend toward the bottom wall 11 of the vessel 13. The inner cylindrical portion 23 and the bottom 24 together constitute the projected portion according to the present invention.

Figure 6:
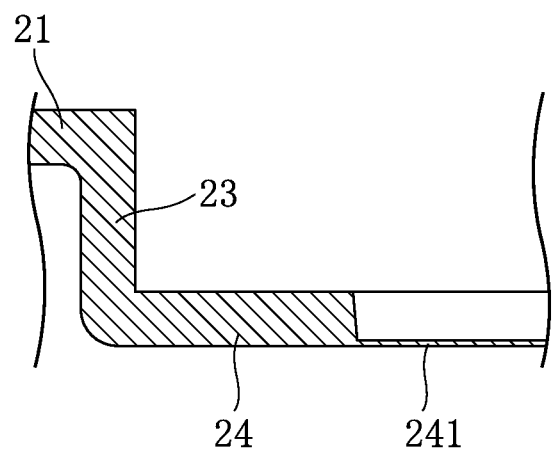
FIG. 6 is a partially enlarged view of FIG. 4.

As shown in FIGS. 4 and 5, in the present embodiment, the bottom 24 is provided with a thin portion 241 at its center. As clearly shown in FIG. 6, the thin portion 241 has a smaller thickness than other portions and is similar to a film. In one example, the thin portion 241 has a thickness of 0.2 to 0.3 mm or so. The thin portion 241 has gas permeability. As viewed in the vertical direction, the thin portion 241 is surrounded by the annular portion 21.

As shown in FIGS. 4 and 5, the presser member 3 is placed on the cover 2 and formed of a hard synthetic resin, example of which include polyvinyl chloride, polypropylene, polyethylene and polystyrene. In the present embodiment, the presser member 3 includes a larger diameter portion 31 having a larger outside diameter and a smaller diameter portion 32 having a smaller outside diameter, with the smaller-diameter portion jointed on top of the outer diameter portion. The presser member 3 has a through-hole 33 that extends in the thickness direction (vertical direction) through the radial center. The through-hole 33 is located inside the side wall 12 as viewed in the vertical direction and thus opens to the thin portion 241 of the cover 2.

As clearly shown in FIGS. 4 and 5, the presser member 3 (the larger diameter portion 31) has a flat lower surface 311. In the assembled state, the annular portion 21 of the cover 2 is in intimate contact with the lower surface 311 of the presser member 3.

As shown in FIGS. 2, 4 and 5, the presser member 3 is provided with grooves 34 formed in the upper surface. In the present embodiment, the smaller diameter portion 32 is made up of three pieces that arranged in a circumferential direction at predetermined intervals. The gaps between adjacent pieces constitute the grooves 34. With this configuration, each groove 34 connects the peripheral edge of the presser member 3 to the through-hole 33.

In the present embodiment, the presser member 3 is constituted of the larger diameter portion 31 and the smaller diameter portion 32 jointed together. Alternatively, the presser member may be integrally formed by resin molding, for example.

The lid 4 is placed on the presser member 3. The lid 4 has a circular disc portion 41 and a skirt portion 42 extending downward from the peripheral edge of the circular disc portion 41. The lid 4 is integrally formed by resin molding, for example. In the case where the culture container 1 is a petri dish, a lid that comes with the petri dish may be used as the lid 4.

The holder 5 is used to hold the culture container 1, the cover 2, the presser member 3 and the lid 4 as stacked (in the assembled state). As shown in FIGS. 2 and 4, the holder 5 includes a flat bottom plate 51, a top plate 52 parallel to the bottom plate 51 and a pair of side plates 53. These plates are joined together to define a closed outline. The pair of side plates 53 are each connected at the opposite ends to the bottom plate 51 and the top plate 52.

The distance from the upper surface of the bottom plate 51 to the lower surface of the top plate 52 is slightly shorter than the height of an assembly formed by simply stacking the culture container 1, the cover 2, the presser member 3 and the lid 4. When the culture container 1, the cover 2, the presser member 3 and the lid 4 are stacked and held together by hand with pressure applied from the top and the bottom of the assembly, the height of the assembly is reduced mainly due to the compression of the annular portion 21. This allows the assembly to be inserted between the bottom plate 51 and the top plate 52 of the holder. When the hand(s) is released, the annular portion 21 having elastic resilience tends to restore its original height. However, such restoration to increase the height is restricted by the bottom plate 51 and the top plate 52. In this state, the assembly of the culture container 1, the cover 2, the presser member 3 and the lid 4 is pressed vertically between the bottom plate 51 and the top plate 52 and thus held integral by the holder 5.

Next, the culture container transporting set A1 is described regarding the usages and advantages.

The culture container transporting set A1 is used for transporting living cells or tissues stored with a culture medium in the culture container 1 (the vessel 13), in a manner to keep them being cultured (cultured-state transportation). The cells or tissues and the culture medium stored in the vessel 13 are not specifically limited.

The cultured cells may be adherent cells, such as iPS cells. During the growth, such cultured cells remain attached to the culture surface (the upper surface of the bottom wall 11) covered with a necessary amount of culture medium. Therefore, during the cultured-state transportation of adherent cells, the culture medium should not be shaken in order to avoid detachment of the adherent cells from the bottom wall 11. To this end, it is necessary to fill the entire volume of the vessel 13 with the culture medium to restrict the migration of the culture medium.

Figure 7:
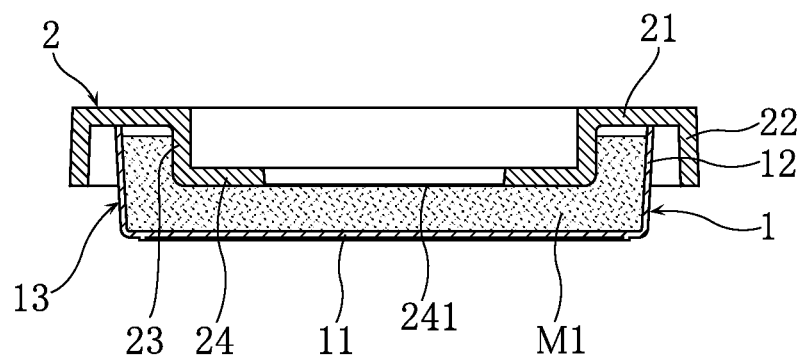
FIG. 7 is a sectional view illustrating a step of introducing a culture medium into a vessel.
Figure 8:
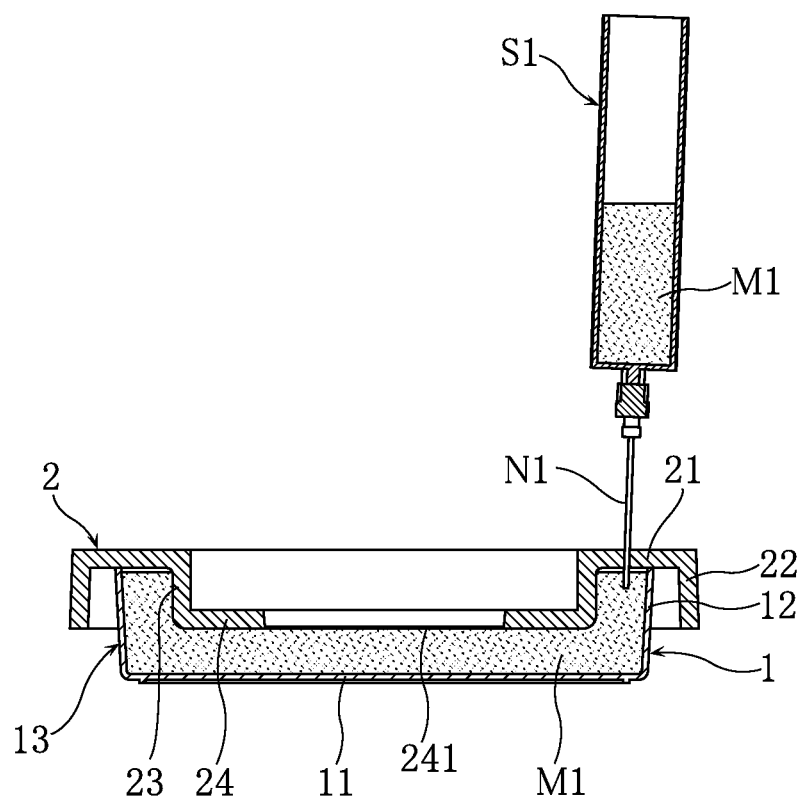
FIG. 8 is a sectional view illustrating a step of introducing the culture medium into the vessel.

The following describes an example of a process of introducing a culture medium into the vessel 13, with reference to FIGS. 7 and 8. First, as shown in FIG. 7, an appropriate amount of culture medium M1 is introduced into the vessel 13, and the cover 2 is placed on the vessel. The culture medium is displaced by the projected portion (the inner cylindrical portion 23 and the bottom 24) of the cover 2. At this stage, the liquid surface of the culture medium M1 is slightly lower than the upper edge of the side wall 12. There is a small space left empty in the volume enclosed by the vessel 13 and the cover 2. Next, as shown in FIG. 8, some more culture medium M1 is injected into the enclosed volume using a syringe S1. This injection of the culture medium M1 is carried out by sticking a syringe needle N1 into the annular portion 21.

Then, the presser member 3 and the lid 4 are placed, and the holder 5 is used to hold the culture container 1, the cover 2, the presser member 3 and the lid 4 in the assembled state. In this way, for the cultured-state transportation, the vessel 13 is filled completely with the culture medium M1 as shown in FIG. 5. Note that the inner cylindrical portion 23 and the bottom 24 located inside the side wall 12 project toward the bottom wall 11. This configuration reduces the volume space available in the vessel 13 for storing a culture medium and so on. Therefore, the amount of culture medium M1 used in the cultured-state transportation is reduced.

The holder 5 holds the culture container 1, the cover 2, the presser member 3 and the lid 4 in the assembled state by applying pressure from the top and the bottom of the assembly. This ensures that the cover 2 forms liquid-tight sealing against the contents of the vessel 13 (cultured cells and culture medium). Consequently, spilling of the contents is prevented despite the vibrations and shocks which may occur during the cultured-state transportation.

As described above, the annular portion 21 of the cover 2 has a re-sealing ability to seal punctures by the syringe needle N1. In the assembled state, the annular portion 21 is in intimate contact with the lower surface 311 of the presser member 3 (the larger diameter portion 31). This prevents leakage of the contents (culture medium, for example) through a syringe needle puncture during the transportation of the culture container transporting set A1.

The annular portion 21 of the cover is in intimate contact with the upper end 121 of the side wall 12. The cover 2 has the thin portion 241 that is gas permeable. The thin portion 241 is surrounded by the annular portion 21 as viewed in the vertical direction. This configuration maintains the contents of the vessel 13 in communication with the atmosphere outside the vessel 13. The present embodiment thus ensures that the contents of the vessel 13 are maintained cultured in a ventilated condition during the transportation.

The presser member 3 is provided with the through-hole 33 located inside the side wall 12 as viewed in the vertical direction. That is, the presser member 3 placed on the cover 2 does not block the thin portion 241, ensuring that the vessel 13 remains in communication with the ambient atmosphere.

The presser member 3 is provided with the grooves 34 formed in the upper surface to connect the peripheral edge of the presser member 3 to the through-hole 33. With this configuration, the through-hole 33 is not closed by the lid 4 or the holder 5, ensuring that the vessel 13 remains in communication with the ambient atmosphere.

The holder 5 has a closed outline defined by the flat bottom plate 51, the top plate 52 parallel to the bottom plate 51 and the pair of side plates 53 each connected at the opposite ends to the bottom plate 51 and the top plate 52. This configuration ensures that the bottom plate 51 and the top plate 52 are separated from each other at a fixed distance. Therefore, when the culture container 1, the cover 2, the presser member 3 and the lid 4 are assembled and attached to the holder 5, the holder 5 holds the assembly with a constant pressure. In this way, the pressure applied by the holder 5 is stable.

After the culture container transporting set A1 is transported, the assembly of the culture container 1, the cover 2, the presser member 3 and the lid 4 is pulled out of the holder 5. Then, the culture container 1, the cover 2, the presser member 3 and the lid 4 can be easily disassembled. More specifically, in the assembled state, the culture container 1, the cover 2, the presser member 3 and the lid 4 are simply stacked on one another. Naturally, the lid 4, the presser member 3 and the cover 2 can be readily removed one by one from the top. This prevents undesirable risk that the contents are spilled from the culture container 1 (the vessel 13) when the cover 2 is removed from the culture container 1.

Figure 9:
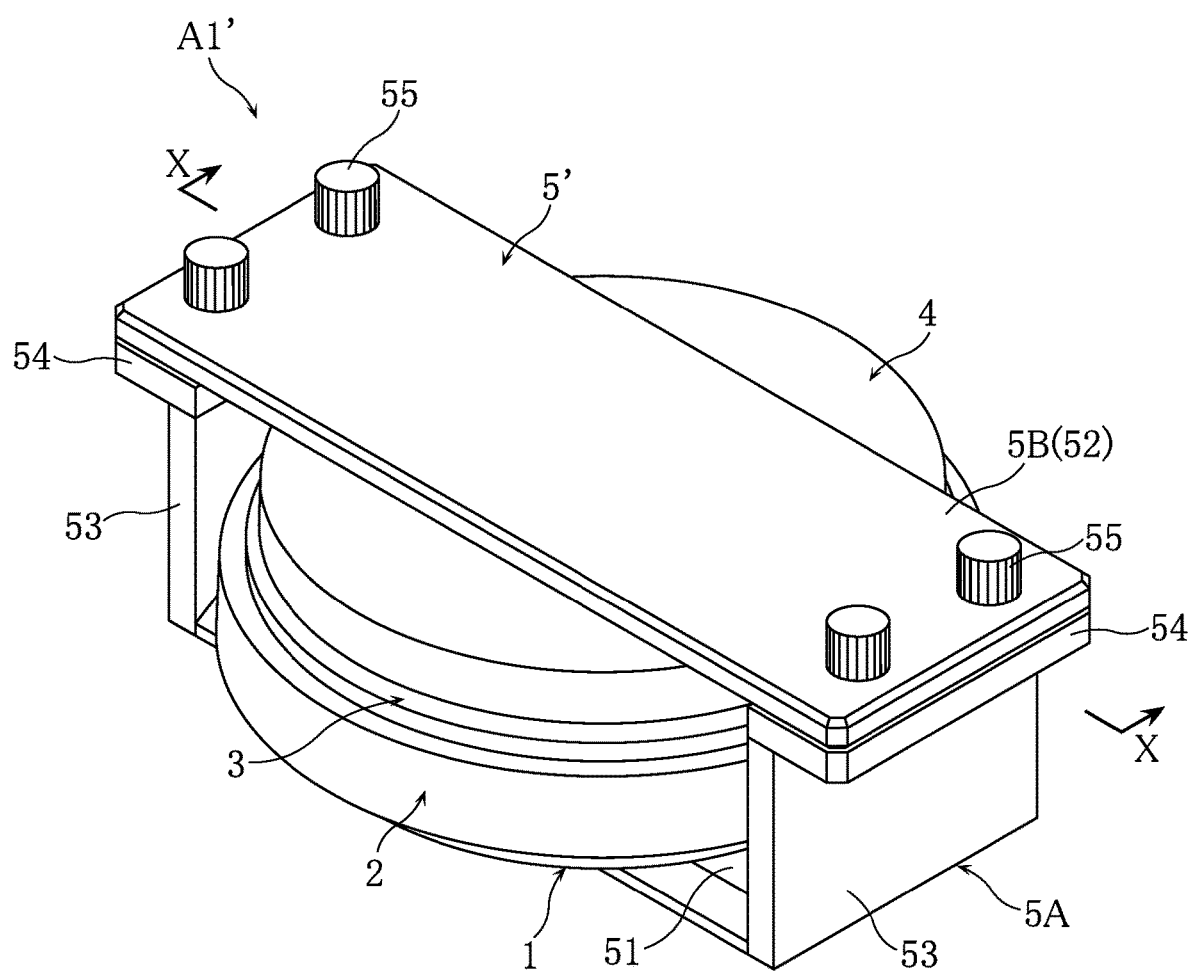
FIG. 9 is a perspective view illustrating a variation of the culture container transporting set shown in FIG. 1.
Figure 10:
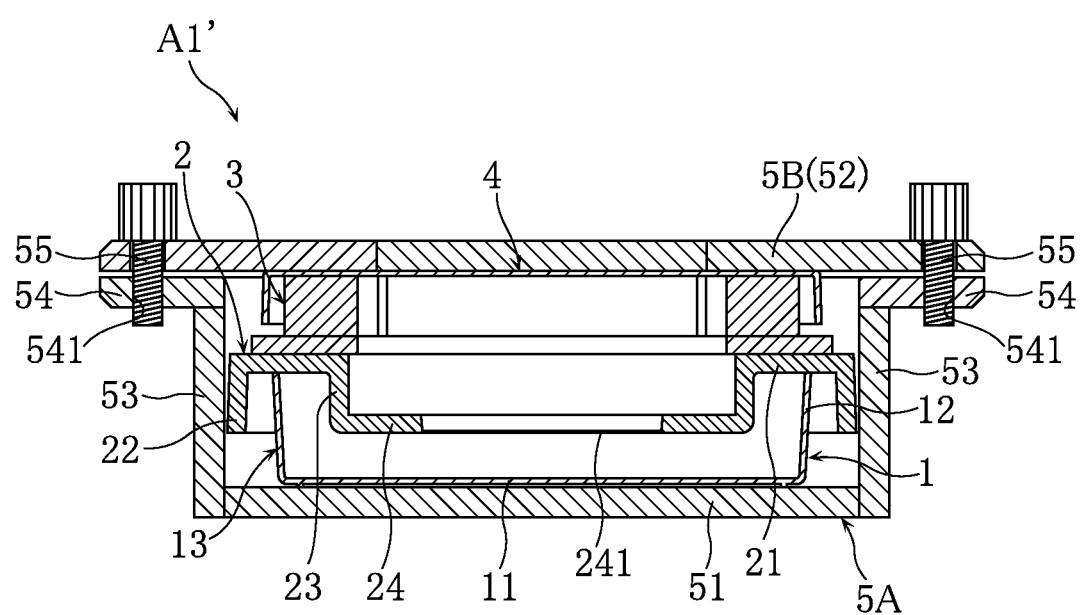
FIG. 10 is a sectional view taken along line X-X in FIG. 9.

FIGS. 9 and 10 show a variation of the culture container transporting set A1 described above. The culture container transporting set A1' shown in the figures differs from the culture container transporting set A1 only in the configuration of the holder.

The culture container transporting set A1' includes a holder 5' constituted of a bottom member 5A and a lid member 5B that is detachable from the bottom member 5A. The bottom member 5A has a flat bottom plate 51, a pair of side plates 53 raised from the opposite ends of the bottom plate 51 and a pair of flanges 54 extending horizontally from the upper end of each side plate. The lid member 5B has a top plate 52 that is parallel to the bottom plate 51. As clearly shown in FIG. 10, each flange 54 is provided with a plurality of screw holes 541 for screw engagement with fastening bolts 55. The fastening bolts 55 fasten the top plate 52 to the pair of flanges 54. In one example, the fastening bolt 55 has a grooved or knurled head to provide extra grip for manual tightening of the head. As can be seen from the figures, with the fastening bolts 55, an adjustment may be made to the separation distance between the bottom plate 51 and the top plate 52. Note that the plurality of fastening bolts 55 constitute the fastening means of the present invention.

The culture container transporting set A1' shown in FIGS. 9 and 10 can achieve advantages similar to those achieved by the culture container transporting set A1 described above. In addition, the holder 5' is usable to adjust the separation distance between the bottom plate 51 and the top plate 52. It is therefore possible to appropriately adjust the pressure applied by the holder 5' to the culture container 1, the cover 2, the presser member 3 and the lid 4 in the assembled state.

Figure 11:
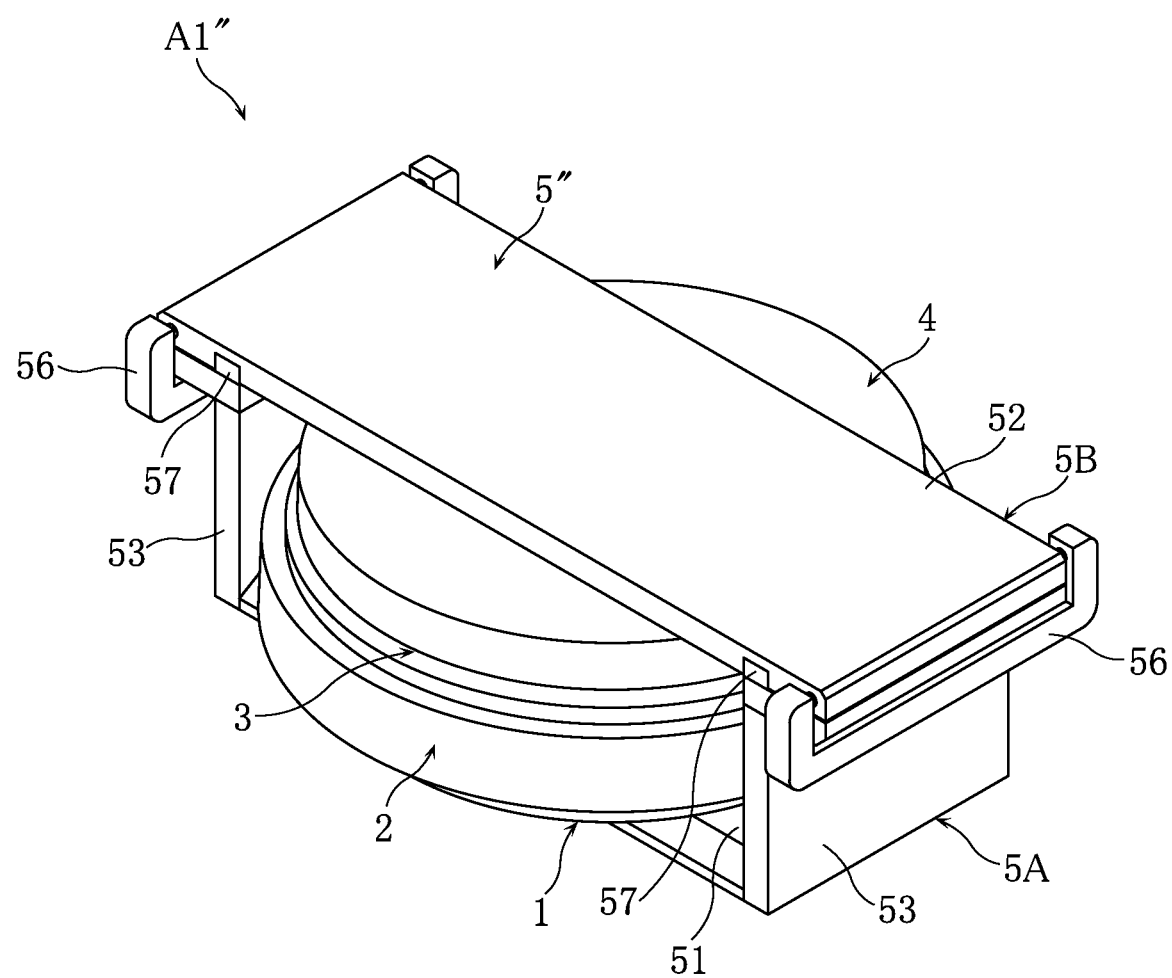
FIG. 11 is a perspective view illustrating another variation of the culture container transporting set shown in FIG. 1.

FIG. 11 shows another variation of the culture container transporting set A1 described above. The culture container transporting set A1" shown in the figure differs from the culture container transporting set A1 described above only in the configuration of the holder.

Figure 12:
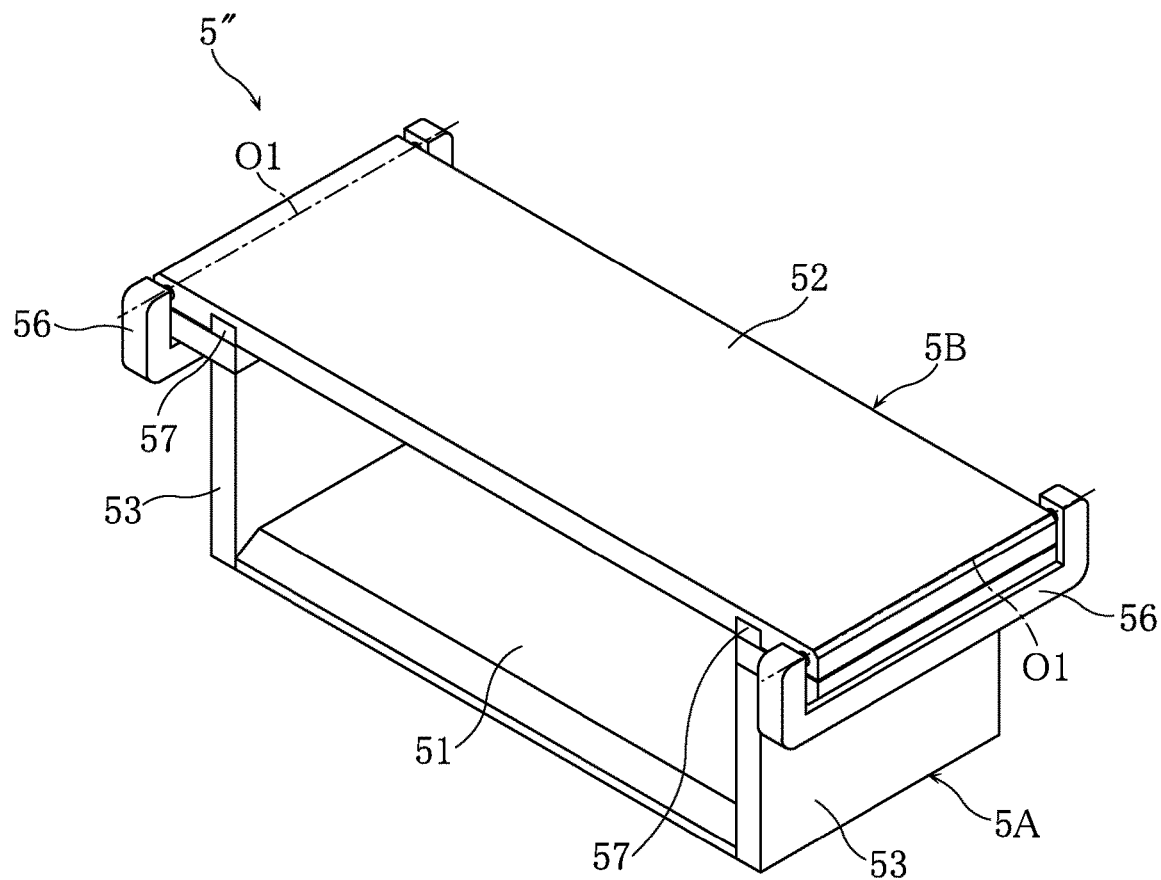
FIG. 12 is a perspective view showing a holder.
Figure 13:
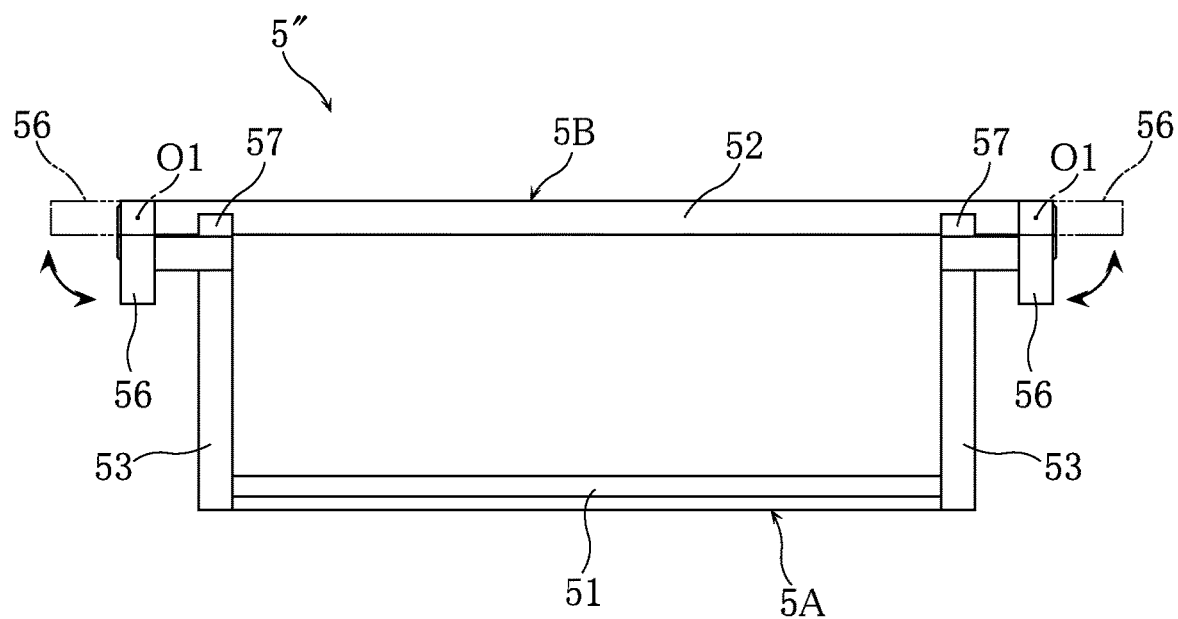
FIG. 13 is a front view of the holder shown in FIG. 12.

The culture container transporting set A1" has a holder 5" having a bottom member 5A and a lid member 5B detachable from the bottom member 5A. The bottom member 5A has a flat bottom plate 51, a pair of side plates 53 raised from the opposite ends of the bottom plate 51, and a pair of flanges 54 extending horizontally from the upper end of each side plate. The lid member 5B has a top plate 52 that is parallel to the bottom plate 51 and also has a pair of hinges 56 provided at the opposite ends of the top plate 52. An elastic material is disposed between the bottom member 5A and the lid member 5B. In this variation, rubber packing 57 is provided in grooves formed in the lower surface of the top plate 52, as shown in FIGS. 11 and 12. Also as shown in FIGS. 11 and 12, each hinge 56 is swingable about a predetermined swing axis O1. As clearly shown in FIG. 12, in a state where the hinges 56 are anchored to the respective flanges, the lid member 5B (the top plate) is urged upward by the elastic resilience of the rubber packing 57. In this state, the upper surface of the bottom plate 51 and the lower surface of the top plate 52 are separated from each other at a fixed distance. In this way, with the configuration shown in FIGS. 11 to 13, the bottom member 5A and the lid member 5B can be fastened by the hinges 56 such that the separation distance between the bottom plate 51 and the top plate 52 is fixed. Note that the pair of hinges 56 constitutes the fastening means according to the present invention.

The culture container transporting set A1" shown in FIG. 11 can achieve advantages similar to those achieved by the culture container transporting set A1 described above. In addition, the holder 5" features the bottom member 5A and the lid member 5B that are detachable from each other. When the culture container 1, the cover 2, the presser member 3 and the lid 4 are assembled and attached to the holder 5", the holder 5" holds the assembly with a constant pressure. This variation therefore ensures that the holder 5" allows easy attachment and detachment, despite that the holder 5" is configured to apply a relatively large pressure for holding.

Figure 14:
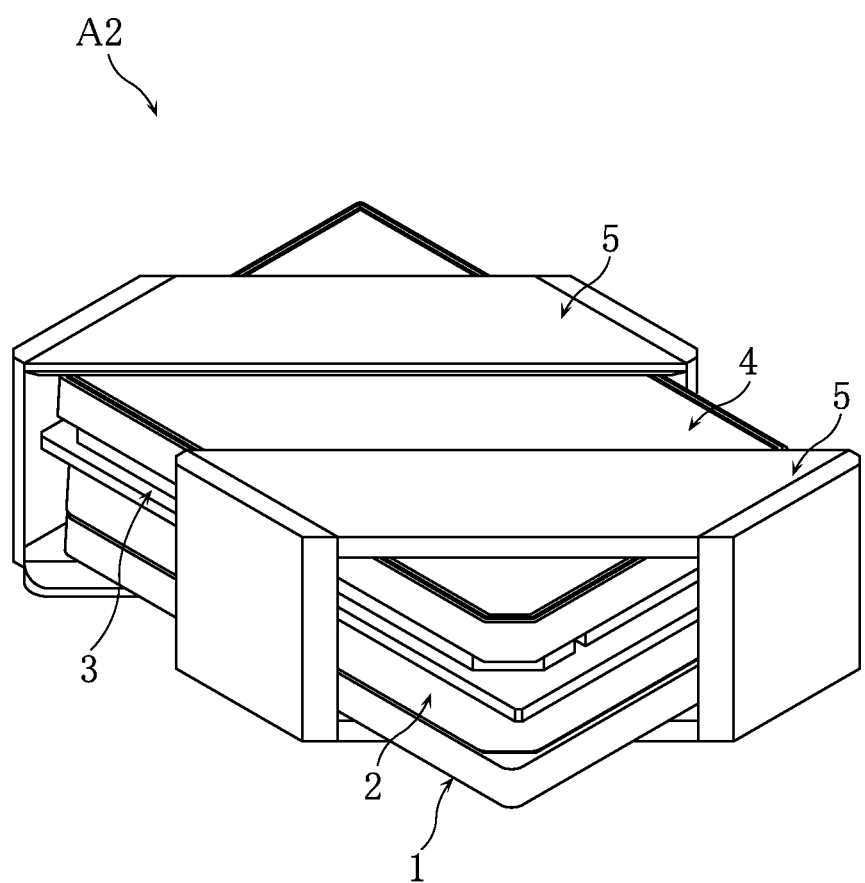
FIG. 14 is a perspective view showing a second embodiment of a culture container transporting set according to the present invention.

FIGS. 14 to 18 show a second embodiment of a culture container transporting set according to the present invention. In FIG. 14 and the subsequent figures, the elements that are identical or similar to those of the foregoing embodiment are designated by the same reference signs as those used for the foregoing embodiment, and the description is omitted appropriately.

Figure 15:
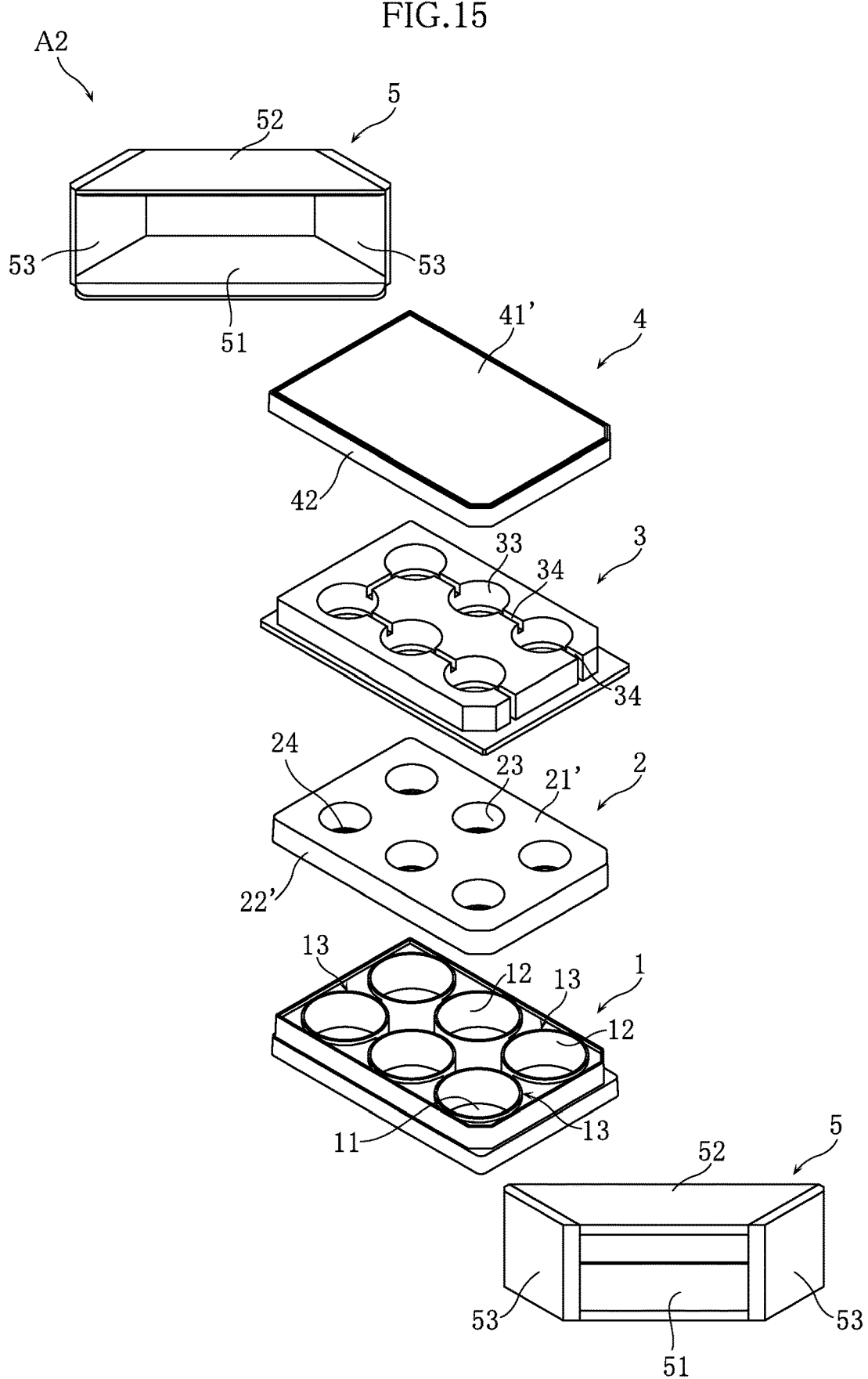
FIG. 15 is an exploded perspective view of the culture container transporting set shown in FIG. 14.
Figure 16:
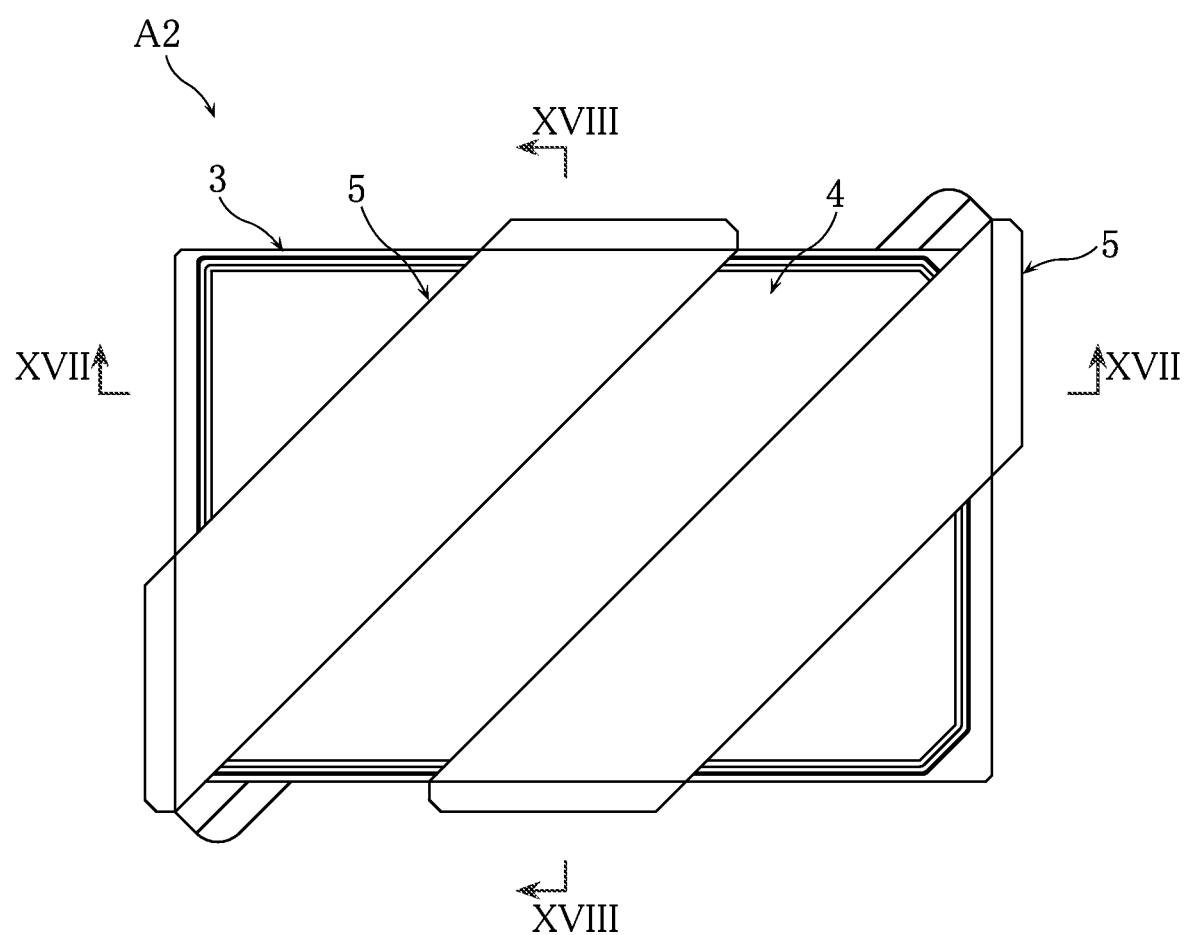
FIG. 16 is a plan view of the culture container transporting set shown in FIG. 14.

The culture container transporting set A2 shown in FIGS. 14 and 15 includes a culture container 1, a cover 2, a presser member 3, a lid 4 and holders 5. FIGS. 14 and 16 to 18 show an assembled state in which the culture container 1, the cover 2, the presser member 3 and the lid 4 are staked. FIG. 15 is a perspective view showing the parts of the culture container transporting set A2 in a disassembled state. In the present embodiment, the culture container 1 is a well plate having a plurality of (six in this embodiment) wells serving as vessels 13. The vessels 13 share a rectangular bottom wall 11 and each have a cylindrical side wall 12 raised at appropriate locations from the bottom wall 11.

Figure 17:
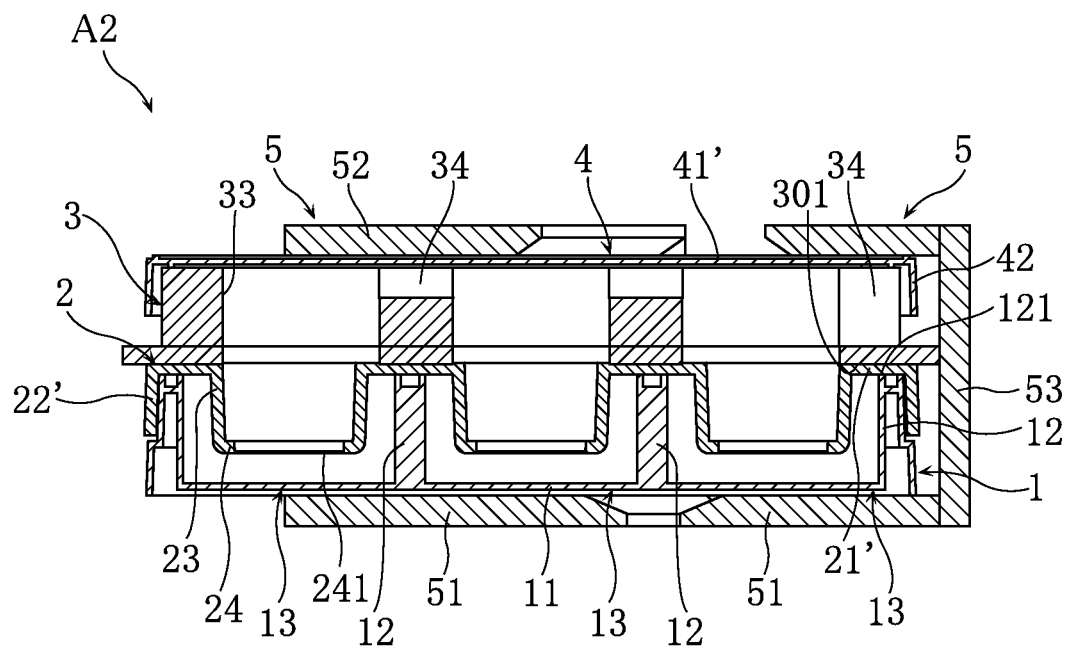
FIG. 17 is a sectional view taken along line XVII-XVII in FIG. 16.
Figure 18:
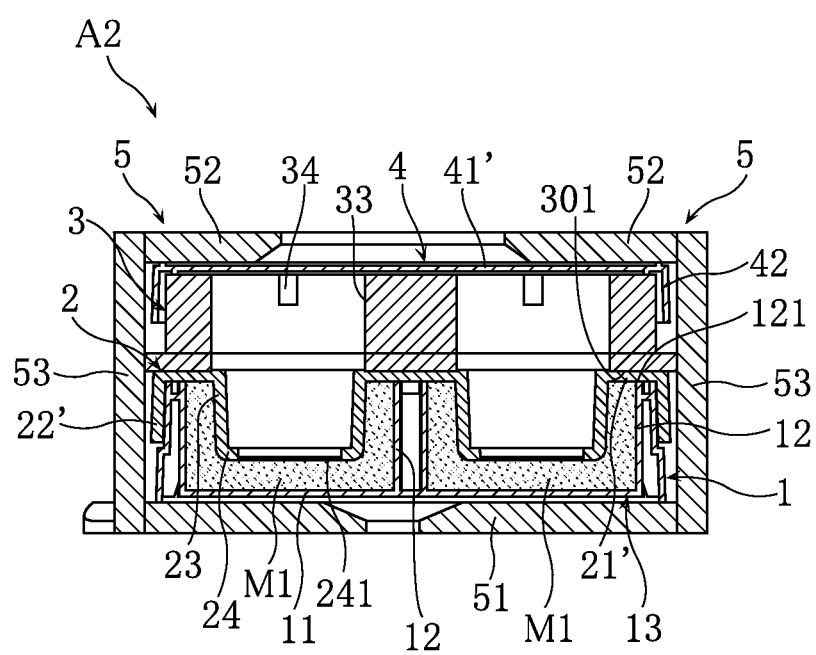
FIG. 18 is a sectional view taken along line XVIII-XVIII of FIG. 16, with contents stored in a vessel.

The cover 2 may be a rubber molded product. As shown in FIGS. 15, 17 and 18, the cover 2 includes a generally rectangular planar portion 21', an outer wall portion 22' extending downward from the peripheral edges of the planner portion 21', a plurality of inner cylindrical portions 23 and a plurality of bottoms 24.

The planar portion 21' is in intimate contact with upper ends 121 of the respective side walls 12 and extends over the side walls 12 to cover a location radially outside and a location radially inside of each side wall. The flat portion 21' has an appropriate thickness and appropriate elastic resilience against the load applied in a vertical direction. In one example, the thickness of the planar portion 21' may be 1 to 3 mm or so. The planar portion 21' corresponds to the thick portion of the present invention. As a result that the planar portion 21' has an appropriate thickness and elastic resilience, the planar portion 21' achieves a re-sealing ability to seal syringe needle punctures.

As shown in FIGS. 17 and 18, the inner cylindrical portions 23 and the respective bottoms 24 are each accommodated inside the side wall 12 of the corresponding vessel 13 and vertically extend toward the bottom wall 11 that is common to the vessels 13. The inner cylindrical portions 23 and the bottoms 24 together constitute projected portions according to the present invention.

As shown in FIGS. 17 and 18, in the present embodiment, each bottom 24 is provided with a thin portion 241 at its center. Each thin portion 241 is similar to a film and has gas permeability. As viewed in the vertical direction, the individual thin portions 241 are surrounded by the planner portion 21'.

As shown in FIGS. 17 and 18, the presser member 3 is placed on the cover 2. In the present embodiment, the presser member 3 is formed by joining two plates having different outer dimensions, one larger than the other. The presser member 3 is provided with a plurality of through-holes 33 each extending in the thickness direction (vertical direction) at an appropriate location. The through-holes 33 are located inside the respective side walls 12 as viewed in the vertical direction and thus open to the respective thin portions 241 of the cover 2.

As clearly shown in FIGS. 17 and 18, the presser member 3 has a flat lower surface 301. In the assembled state, the planar portion 21' of the cover 2 is in intimate contact with the lower surface 301 of the presser member 3.

As shown in FIGS. 15, 17 and 18, the presser member 3 is provided with grooves 34 at appropriate locations in the upper surface. In the present embodiment, the grooves 34 are provided to connect adjacent through-holes 33 and also connect the through-holes 33 to the peripheral edges of the presser member 3. In the present embodiment, the presser member 3 is constituted of two plates joined together. Alternatively, the presser member may be integrally formed by resin molding, for example.

The lid 4 is placed on the presser member 3. The lid 4 includes a rectangular planar portion 41' and a skirt portion 42 extending downward from the peripheral edges of the planar portion 41'. The lid 4 is integrally formed by resin molding, for example. In the case where the culture container 1 is a well plate, a lid that comes with the well plate may be used as the lid 4.

The holders 5 are used to hold the culture container 1, the cover 2, the presser member 3 and the lid 4 as stacked (in the assembled state). As shown in FIG. 15, each holder 5 includes a flat bottom plate 51, a top plate 52 parallel to the bottom plate 51 and a pair of side plates 53. These plates are joined together to define a closed outline. The pair of side plates 53 are each connected at the opposite ends to the bottom plate 51 and the top plate 52. Specifically, two holders 5 are provided for the culture container transporting set A2 according to the present embodiment.

The distance from the upper surface of the bottom plate 51 to the lower surface of the top plate 52 is slightly shorter than the height of an assembly formed by simply stacking the culture container 1, the cover 2, the presser member 3 and the lid 4. When the culture container 1, the cover 2, the presser member 3 and the lid 4 are stacked and held together by hand with pressure applied from the top and the bottom of the assembly, the height of the assembly is reduced mainly due to the compression of the planar portion 21'. This allows the assembly to be inserted between the bottom plate 51 and the top plate 52 of each holder. When the hand(s) is released, the planar portion 21' having elastic resilience tends to restore its original height. However, such restoration to increase the height is restricted by the bottom plates 51 and the top plates 52. In this state, the assembly of the culture container 1, the cover 2, the presser member 3 and the lid 4 is pressed vertically by the bottom plate 51 and the top plate 52 of each holder 5 and thus held integral.

Next, the culture container transporting set A2 is described regarding the usages and advantages.

The culture container transporting set A2 is used for transporting living cells or tissues stored with a culture medium in the culture container 1 (the vessels 13), in a manner to keep them being cultured (cultured-state transportation). The cells or tissues and the culture medium stored in the vessels 13 are not specifically limited.

The cultured cells may be adherent cells, such as iPS cells. During the growth, such cultured cells remain attached to the culture surface (the upper surface of the bottom wall 11) covered with a necessary amount of culture medium. Therefore, during the cultured-state transportation of adherent cells, the culture medium should not be shaken in order to avoid detachment of the adherent cells from the bottom wall 11. To this end, it is necessary to fill the entire volume of each vessel 13 with the culture medium to restrict the migration of the culture medium.

The vessels 13 may be filled with a culture medium through the process similar to that described with reference to FIGS. 7 and 8 for the culture container transporting set A1 according to the earlier embodiment. That is, each vessel 13 is first charged with an appropriate amount of culture medium and covered with the cover 2. Then, some more culture medium is injected into the respective vessels 13 using a syringe to completely fill the volume enclosed with the cover 2. This injection is carried out by sticking a syringe needle into the planar portion 21'.

Then, the presser member 3 and the lid 4 are placed, and the holders 5 are used to hold the culture container 1, the cover 2, the presser member 3 and the lid 4 in the assembled state. In this way, for the cultured-state transportation, each vessel 13 is filled completely with the culture medium as shown in FIG. 18. Note that the inner cylindrical portions 23 and the bottoms 24 located inside the respective side walls 12 project toward the bottom wall 11. This configuration reduces the volume space available in each vessel 13 for storing a culture medium and so on. Therefore, the amount of the culture medium M1 used in the cultured-state transportation is reduced.

Note, in addition, that, the holders 5 hold the culture container 1, the cover 2, the presser member 3 and the lid 4 in the assembled state, with pressure applied from the top and the bottom of the assembly. This ensures that the cover 2 forms liquid-tight sealing against the contents of the vessels 13 (cultured cells and culture medium). Consequently, spilling of the contents is prevented despite the vibrations and shocks which may occur during the cultured-state transportation.

Also as described above, the planar portion 21' of the cover 2 has a re-sealing ability to seal punctures by a syringe needle. In addition, in the assembled state, the planar portion 21' is in intimate contact with the lower surface 301 of the presser member 3. This prevents leakage of the contents (culture medium, for example) through a syringe needle puncture during the transportation of the culture container transporting set A2.

In addition, planar portion 21' of the cover 2 is in intimate contact with the upper end 121 of each side wall 12. The cover 2 has the thin portions 241 each of which is gas permeable. The individual thin portions 241 are surrounded by the planner portion 21' as viewed in the vertical direction. This configuration maintains the contents of each vessel 13 in communication with the atmosphere outside the vessel 13. The present embodiment thus ensures that the contents of each vessel 13 are maintained cultured in a ventilated condition during the transportation.

The presser member 3 is provided with the through-holes 33 located inside the respective side walls 12 as viewed in the vertical direction. That is, the presser member 3 placed on the cover 2 does not block the thin portions 241, ensuring that the vessels 13 are in communication with the ambient atmosphere.

The presser member 3 is provided with the grooves 34 formed in the upper surface to connect the peripheral edges of the presser member 3 to the through-holes 33. With this configuration, the through-holes 33 are not closed by the lid 4 or the holders 5, ensuring that the vessels 13 remain in communication with the ambient atmosphere.

Each holder 5 has a closed outline defined by the flat bottom plate 51, the top plate 52 parallel to the bottom plate 51 and the pair of side plates 53 each connected at the opposite ends to the bottom plate 51 and the top plate 52. This configuration ensures that the bottom plate 51 and the top plate 52 are separated from each other at a fixed distance. Therefore, when the culture container 1, the cover 2, the presser member 3 and the lid 4 are assembled and attached to the holders 5, the holders 5 hold the assembly with a constant pressure. In this manner, the pressure applied by the holders 5 is stable.

After the culture container transporting set A2 is transported, the assembly of the culture container 1, the cover 2, the presser member 3 and the lid 4 is pulled out of the holders 5. Then, the culture container 1, the cover 2, the presser member 3 and the lid 4 can be easily disassembled. More specifically, in the assembled state, the culture container 1, the cover 2, the presser member 3 and the lid 4 are simply stacked on one another. Naturally, the lid 4, the presser member 3 and the cover 2 can be readily removed one by one from the top. This prevents undesirable risk that the contents are spilled from the culture container 1 (the vessels 13) when the cover 2 is removed from the culture container 1.

Figure 19:
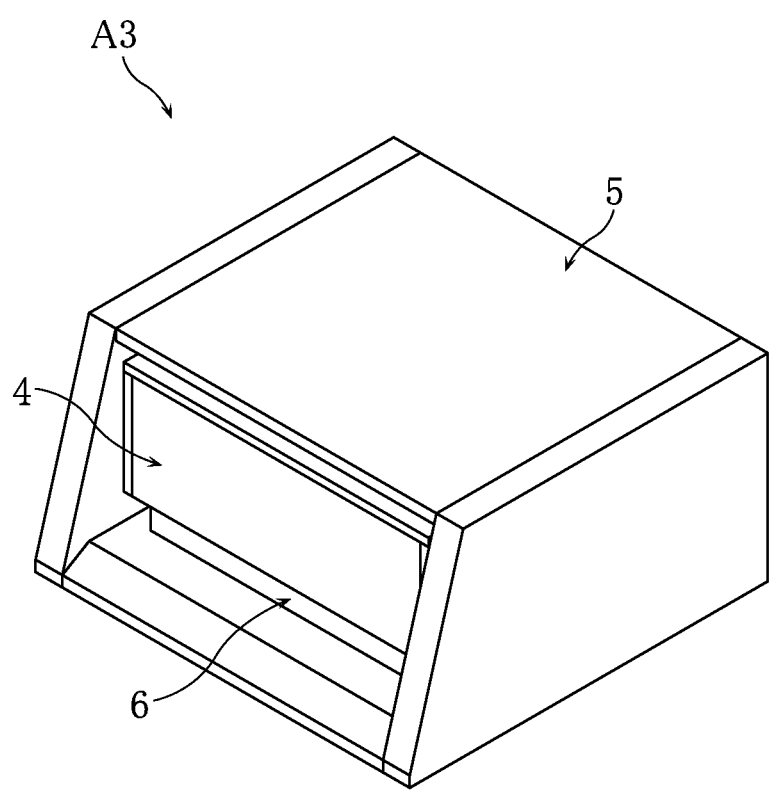
FIG. 19 is a perspective view showing a third embodiment of a culture container transporting set according to the present invention.
Figure 20:
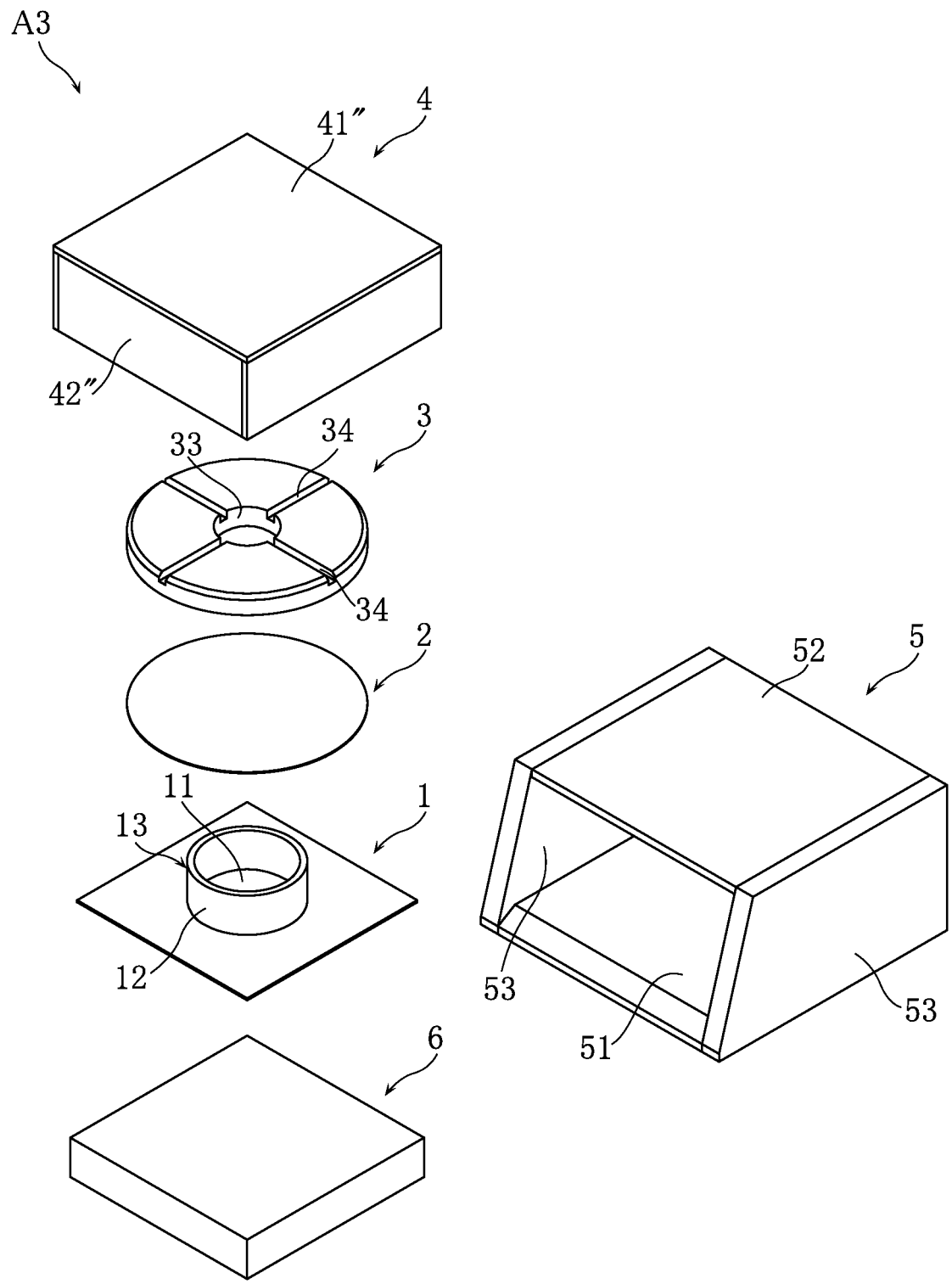
FIG. 20 is an exploded perspective view of the culture container transporting set shown in FIG. 19.
Figure 21:
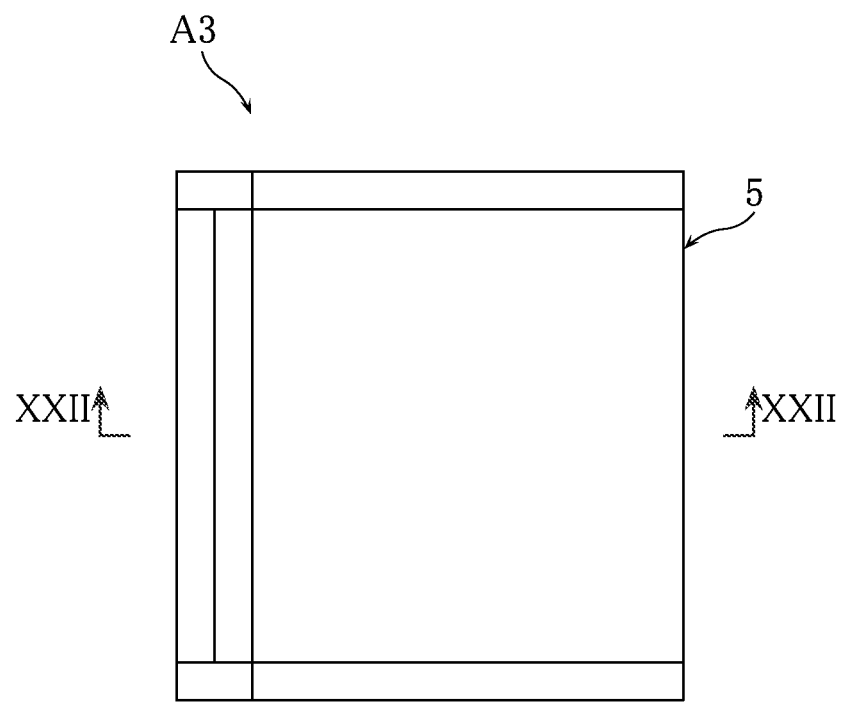
FIG. 21 is a plan view of the culture container transporting set shown in FIG. 19.
Figure 22:
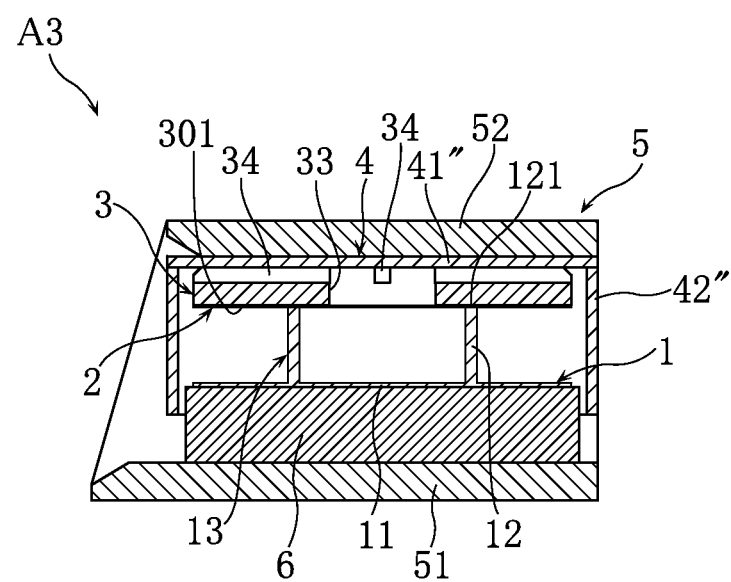
FIG. 22 is a sectional view taken along line XXII-XXII in FIG. 21.

FIGS. 19 to 22 show a third embodiment of a culture container transporting set according to the present invention. The culture container transporting set A3 shown in FIGS. 19 and 20 includes a culture container 1, a cover 2, a presser member 3, a lid 4, a sheet member 6 and a holder 5. FIGS. 19, 21 and 22 show an assembled state in which the sheet member 6, the culture container 1, the cover 2, the presser member 3 and the lid 4 are staked. FIG. 20 is a perspective view showing the parts of the culture container transporting set A3 in a disassembled state.

In the present embodiment, the culture container 1 is a probe and has one vessel 13 constituted of a bottom wall 11 which is a thin and rectangular plate and a cylindrical side wall 12 raised from a central portion of the bottom wall. The bottom wall 11 and the side wall 12 are formed of a non-conductive material, such as glass. Although no details are illustrated or described, the bottom wall 11 is provided with electrodes for measurement, terminals for connection, and so on, at appropriate locations.

The cover 2 is formed of a flexible material having a uniform thickness. Preferably, in addition, the cover 2 is self-adhesive. The cover 2 may be formed of silicone rubber, natural rubber, urethane rubber or elastomer resin, among which silicone rubber is preferable. In view of potential contact between the cover 2 and the contents of the culture container 1 (cultured cells and culture medium), the cover 2 is more preferably formed of a medical grade silicone rubber, which is without cytotoxicity and has biocompatibility. With respect to the hardness, the cover 2 preferably has a rubber hardness of 20 to 40 degrees or so. The cover 2 is similar to a film, for example, and has gas permeability. In one example, the cover 2 has a thickness of 0.2 to 0.3 mm or so.

As shown in FIG. 22, the presser member 3 is placed on the cover 2. In the present embodiment, the presser member 3 is generally in the form of a circular disc. The presser member 3 is provided with a through-hole 33 extending in the thickness direction (vertical direction) at an appropriate location. The through-hole 33 is located inside the side wall 12 as viewed in the vertical direction and thus opens to the cover 2. The presser member 3 has a flat lower surface 301. In the assembled state, the lower surface of the cover 2 is in intimate contact with the upper end 121 of the side wall.

As shown in FIGS. 20 and 22, the presser member 3 is provided with grooves 34 at appropriate locations in the upper surface. In the present embodiment, a plurality of grooves 34 are provided and each groove extends radially from the peripheral edge of the presser member 3 to the through-hole 33.

The lid 4 is placed on the presser member 3. The lid 4 includes a rectangular planar portion 41" and a skirt portion 42" extending downward from the peripheral edges of the planar portion 41". The lid 4 is integrally formed by resin molding, for example. As clearly shown in FIG. 22, in the assembled state, the skirt portion 42" covers the entirety of the side surfaces of the bottom wall 11 of the culture container 1 and a part of the side surfaces of the sheet member 6. Note that the skirt portion 42" corresponds to the side-surface cover of the present invention.

In the present embodiment, in the assembled state clearly shown in FIG. 22, the sheet member 6 is positioned lowest, and the culture container 1 is placed on the sheet member 6. The sheet member 6 is formed of a flexible material having a uniform thickness. The sheet member 6 may be formed of a form material, examples of which include polyethylene foam, urethane foam and silicone foam. The sheet member 6 has an appropriate thickness and an ability to return to its original shape against the load applied in a vertical direction. In one example, the sheet member 6 has a thickness of 5 to 20 mm or so.

The holder 5 is used to hold the sheet member 6, the culture container 1, the cover 2, the presser member 3 and the lid 4 as stacked (in the assembled state). As shown in FIG. 20, the holder 5 includes a flat bottom plate 51, a top plate 52 parallel to the bottom plate 51 and a pair of side plates 53. These plates are joined together to define a closed outline. The pair of side plates 53 are each connected at the opposite ends to the bottom plate 51 and the top plate 52.

The distance from the upper surface of the bottom plate 51 to the lower surface of the top plate 52 is slightly shorter than the height of an assembly formed by simply stacking the sheet member 6, the culture container 1, the cover 2, the presser member 3 and the lid 4. When the sheet member 6, the culture container 1, the cover 2, the presser member 3 and the lid 4 are stacked and held together by hand with pressure applied from the top and the bottom of the assembly, the height of the assembly is reduced mainly due to the compression of the sheet member 6. This allows the assembly to be inserted between the bottom plate 51 and the top plate 52 of the holder. When the hand(s) is released, the sheet member 6 having elastic resilience tends to restore its original height. However, such restoration to increase the height is restricted by the bottom plate 51 and the top plate 52. In this state, the assembly of the sheet member 6, the culture container 1, the cover 2, the presser member 3 and the lid 4 is pressed vertically between the bottom plate 51 and the top plate 52 and thus held integral by the holder 5.

Next, the culture container transporting set A3 is described regarding the advantages.

The culture container transporting set A3 is used for transporting living cells or tissues stored with a culture medium in the culture container 1 (the vessel 13), in a manner to keep them being cultured (cultured-state transportation). The cells or tissues and the culture medium stored in the vessel 13 are not specifically limited.

The holder 5 holds the sheet member 6, the culture container 1, the cover 2, the presser member 3 and the lid 4 in the assembled state, with pressure applied from the top and the bottom of the assembly. This ensures that the cover 2 forms liquid-tight sealing against the contents of the vessel 13 (cultured cells and culture medium). Consequently, spilling of the contents is prevented despite the vibrations and shocks which may occur during the cultured-state transportation.

The cover 2 is in intimate contact with the upper end 121 of the side wall 12. In addition, the cover 2 is gas permeable. This configuration maintains the contents of the vessel 13 in communication with the atmosphere outside the vessel 13. The present embodiment thus ensures that the contents of the vessel 13 are maintained cultured in a ventilated condition during the transportation.

The presser member 3 is provided with the through-hole 33 located inside the side wall 12 as viewed in the vertical direction. That is, the presser member 3 placed on the cover 2 does not obstruct the ventilation of the cover 2, ensuring that the vessel 13 remains in communication with the ambient atmosphere.

The presser member 3 is provided with the grooves 34 formed in the upper surface to connect the peripheral edge of the presser member 3 to the through-hole 33. With this configuration, the through-hole 33 is not closed by the lid 4 or the holder 5, ensuring that the vessel 13 remains in communication with the ambient atmosphere.

The holder 5 has a closed outline defined by the flat bottom plate 51, the top plate 52 parallel to the bottom plate 51 and the pair of side plates 53 each connected at the opposite ends to the bottom plate 51 and the top plate 52. This configuration ensures that the bottom plate 51 and the top plate 52 are separated from each other at a fixed distance. Therefore, when the sheet member 6, the culture container 1, the cover 2, the presser member 3 and the lid 4 are assembled and attached to the holder 5, the holder 5 holds the assembly with a constant pressure. In this way, the pressure applied by the holder 5 is stable.

In addition, when the sheet member 6, the culture container 1, the cover 2, the presser member 3 and the lid 4 are in the assembled state, the skirt portion 42″ of the lid 4 covers the entirety of the side surfaces of the bottom wall 11 of the culture container 1 and a part the side surfaces of the sheet member 6. This configuration allows the assembly, in which the sheet member 6, the culture container 1, the cover 2, the presser member 3 and the lid 4 are stacked, to be handled by gripping the side surfaces of the lid 4 (the skirt portion 42″) and the side surfaces of the sheet member 6. More specifically, the assembly can be handled without having to directly touching by hand the glass that forms the bottom wall 11 of the culture container 1. Such handling is preferable in terms of safety.

After the culture container transporting set A3 is transported, the assembly of the sheet member 6, the culture container 1, the cover 2, the presser member 3 and the lid 4 is pulled out of the holder 5. Then, the sheet member 6, the culture container 1, the cover 2, the presser member 3 and the lid 4 can be easily disassembled. More specifically, in the assembled state, the sheet member 6, the culture container 1, the cover 2, the presser member 3 and the lid 4 are simply stacked on one another. Naturally, the lid 4, the presser member 3 and the cover 2 can be readily removed one by one from the top. This prevents undesirable risk that the contents are spilled from the culture container 1 (the vessel 13) when the cover 2 is removed from the culture container 1.

Figure 23:
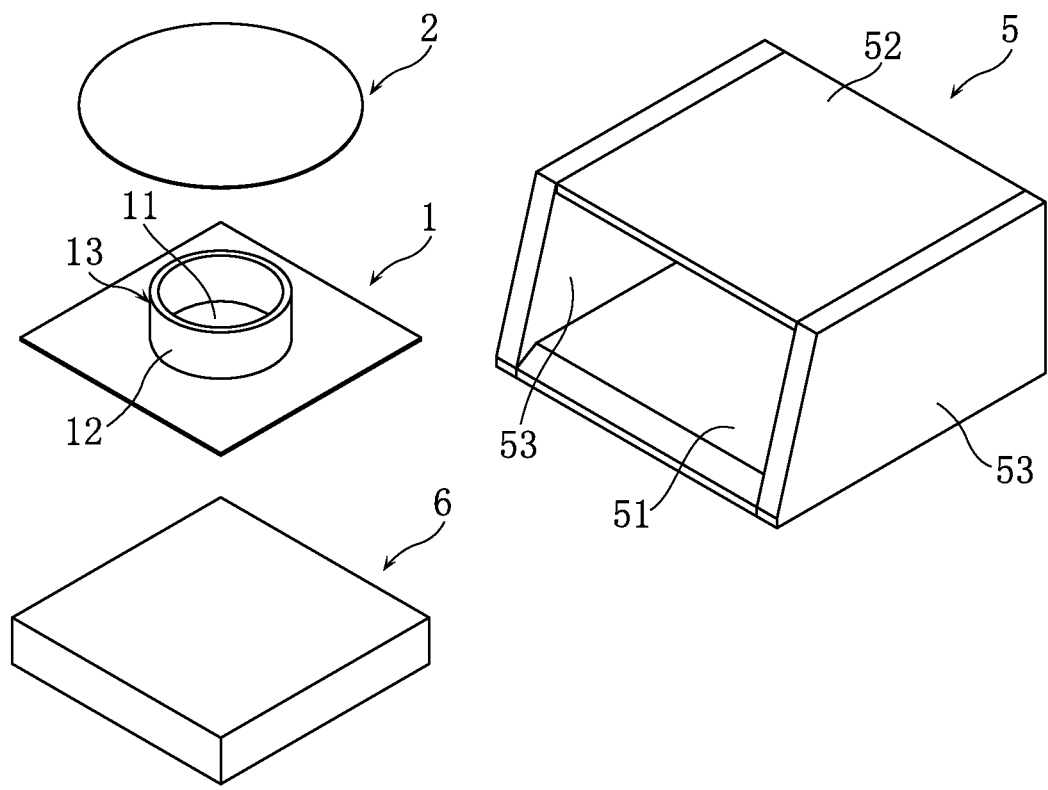
FIG. 23 is an exploded perspective view showing a variation of the culture container transporting set shown in FIG. 19.
Figure 24:
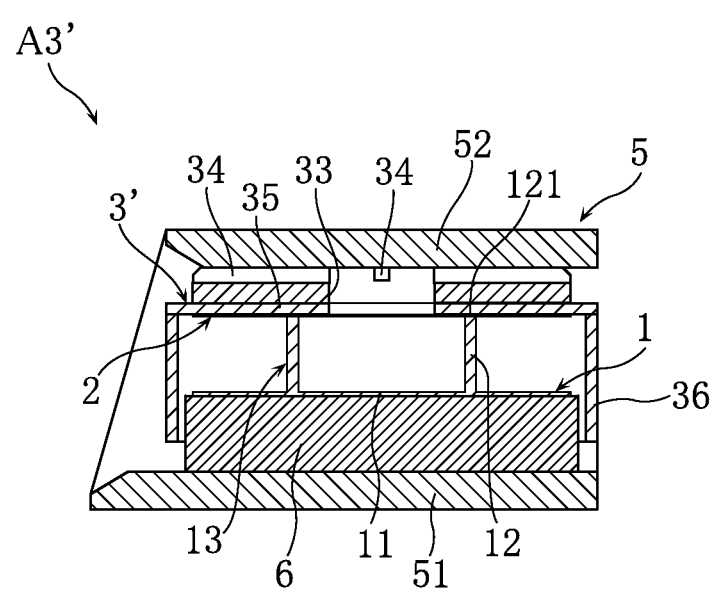
FIG. 24 is a sectional view of the culture container transporting set shown in FIG. 23, taken in a manner similar to FIG. 22.

FIGS. 23 and 24 show a variation of the culture container transporting set A3 described above. The culture container transporting set A3′ shown in the figures includes a presser member 3′, instead of the presser member 3 and the lid 4 of the culture container transporting set A3 described above. The presser member 3′ into which the presser member and the lid are integrated constitutes the only difference with the culture container transporting set A3.

In the culture container transporting set A3′, the presser member 3′ has a rectangular planar portion 35 and a skirt portion 36 extending downward from the peripheral edges of the planar portion 35. The presser member 3′ is integrally formed by resin molding, for example. As clearly shown in FIG. 24, in the assembled state, the skirt portion 36 covers the entirety of the side surfaces of the bottom 11 of the culture container 1 and a part of the side surfaces of the sheet member 6. Note that the skirt portion 36 corresponds to the side-surface cover of the present invention.

The culture container transporting set A3′ shown in FIGS. 23 and 24 can achieve advantages similar to those achieved by the culture container transporting set A3 described above. In addition, the assembly in which the sheet member 6, the culture container 1, the cover 2 and the presser member 3′ are stacked can be handled by gripping the side surfaces of the skirt portion 36 and the side surfaces of the sheet member 6. More specifically, the assembly can be handled without having to directly touching by hand the glass that forms the bottom wall 11 of the culture container 1. Such handling is preferable in terms of safety.

Figure 25:
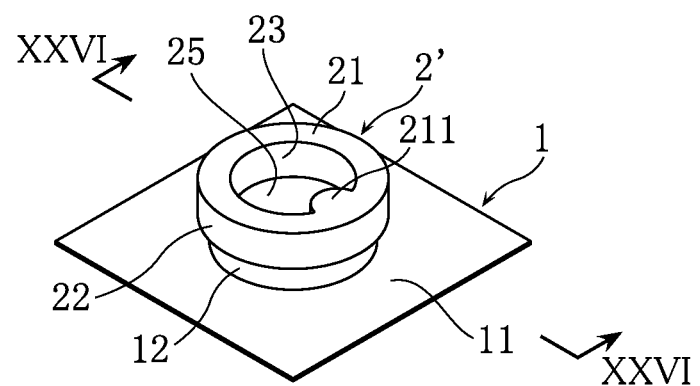
FIG. 25 is a perspective view illustrating a variation of a cover included in the culture container transporting set shown in FIG. 19.
Figure 26:
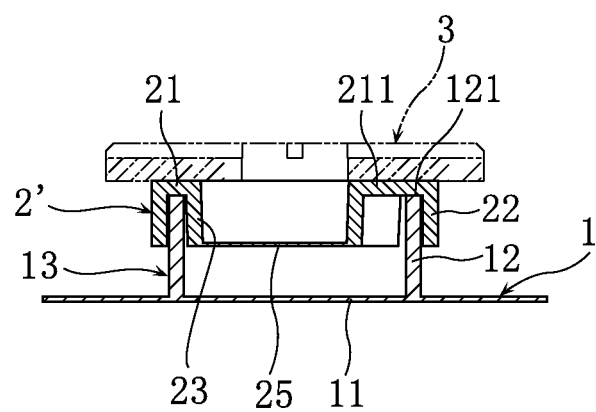
FIG. 26 is a sectional view taken along line XXVI-XXVI in FIG. 25.

FIGS. 25 and 26 show a variation of the culture container transporting set A3 described above. The cover 2′ shown in the figures may be a rubber molded product, rather than the cover 2 formed of a film as in the culture container transporting set A3.

The cover 2′ includes a planar annular portion 21, an outer cylindrical portion 22 extending downward from the outer peripheral edge of the annular portion 21, an inner cylindrical portion 23 extending downward from the inner peripheral edge of the annular portion 21, and a thin bottom 25 closing the lower end of the inner cylindrical portion 23. The annular portion 21 is in intimate contact with the upper end 121 of the side wall 12 and extends over the side wall 12 to cover a location radially outside and a location radially inside the side wall. The annular portion 21 has an appropriate thickness and appropriate elastic resilience against the load applied in the vertical direction. In one example, the thickness of the annular portion 21 may be 1 to 3 mm or so. The annular portion 21 corresponds to the thick portion of the present invention. As a result that the annular portion 21 has an appropriate thickness and elastic resilience, the annular portion 21 achieves a re-sealing ability to seal syringe needle punctures.

In the cover 2' shown in FIGS. 25 and 26, the inner cylindrical portion 23 and the thin bottom 25 are accommodated inside the side wall 12 of the vessel 13 and vertically extend toward the bottom wall 11 of the vessel 13. The inner cylindrical portion 23 and the thin bottom 25 together constitute the projected portion according to the present invention. In addition, the annular portion 21 of the cover 2' has a bulge 211 that bulges radially inward.

As clearly shown in FIG. 26, the thin bottom 25 has a smaller thickness than other portions and is similar to a film. In one example, the thin bottom 25 has a thickness of 0.2 to 0.3 mm or so. The thin bottom 25 has gas permeability. As viewed in the vertical direction, the thin bottom 25 is surrounded by the annular portion 21.

The cultured cells may be adherent cells, such as iPS cells. During the growth, such cultured cells remain attached to the culture surface (the upper surface of the bottom wall 11) covered with a necessary amount of culture medium. Therefore, during the cultured-state transportation of adherent cells, the culture medium should not be shaken in order to avoid detachment of the adherent cells from the bottom wall 11. To this end, it is necessary to completely fill the vessel 13 with the culture medium to restrict the migration of the culture medium.

Figure 27:
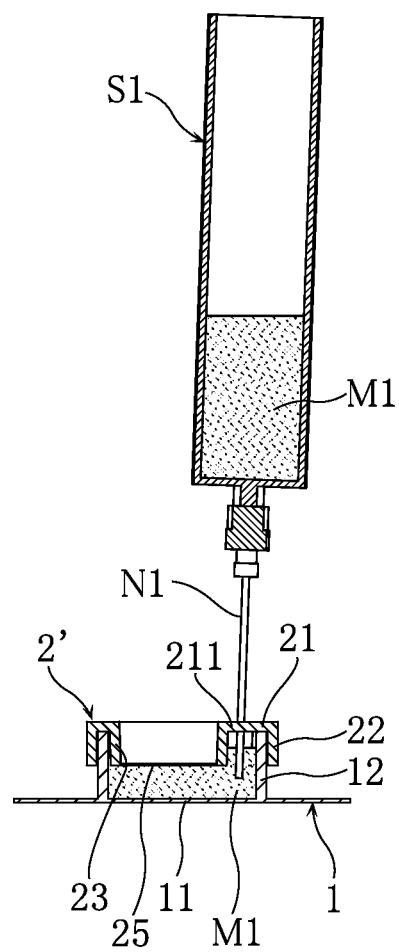
FIG. 27 is a sectional view illustrating a step of introducing a culture medium into a vessel.

The vessel 13 may be filled with a culture medium through the process similar to that described with reference to FIGS. 7 and 8 for the culture container transporting set A1 according to the earlier embodiment. That is, the vessel 13 is first charged with an appropriate amount of culture medium and covered with the cover 2. Then, as shown in FIG. 27, some more culture medium M1 is injected into the vessel 13 using a syringe S1 to completely fill the volume enclosed by the vessel 13 and the cover 2. This injection of the culture medium M1 is carried out by sticking a syringe needle N1 into the bulge 211. In this way, the vessel 13 is filled completely with the culture medium M1 for the cultured-state transportation. Note that the inner cylindrical portions 23 and the thin bottom 25 located inside the side wall 12 project toward the bottom wall 11. This configuration reduces the volume space available in the vessel 13 for storing a culture medium and so on. In other words, the provision of the cover 2' is effective to reduce the amount of the culture medium M1 used for the cultured state transportation.

Although the embodiments of the present invention have been described above, the scope of the present invention is not limited to the above-described embodiments, and all variations within the scope of the matters described in each claim are included in the scope of the present invention.

Figure 28:
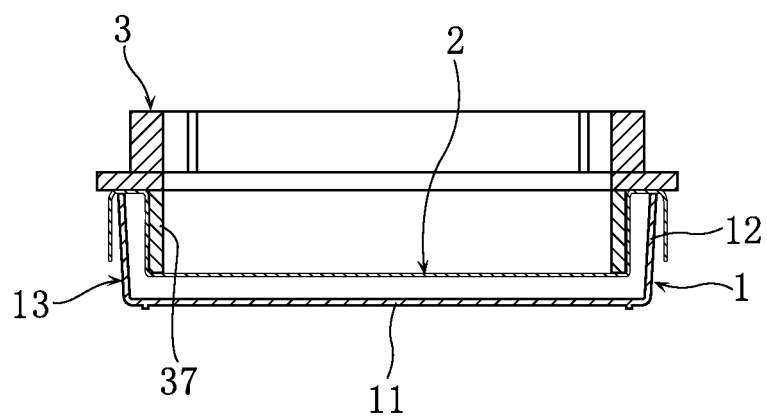
FIG. 28 is a sectional view showing a presser member and a cover having another configuration.

In the embodiments described above, the cover is formed of rubber or elastomer resin, but the configuration of the cover is not limited to this. The cover 2 may be constituted of a resin film, which may have gas permeability and no definite shape. Such a resin film may be formed of polymethyl pentene mixed with olefin or of polyvinylidene chloride. In a case where the cover is constituted of a resin film having no definite shape, the presser member 3 may be formed with a tubular portion 37 as shown in FIG. 28. The tubular portion 37 is accommodate inside the side wall 12 and extends downward toward the bottom wall 11. With this configuration, in a state where the presser member 3 is placed on the cover 2, the tubular portion 37 of the cover 2 projects toward the bottom wall 11. This configuration reduces the volume space available in the vessel 13 for storing a culture medium and so on. Therefore, the amount of culture medium used in the cultured-state transportation is reduced.

Alternatively, the cover may be formed of a sheet material that is relatively large and uniform thickness. Although without gas permeability, such an inexpressive sheet material is duly usable for short-term transportation to enable the holder to hold the assembly under pressure and to seal the culture container 1 liquid tight. Therefore, this alternative is effective for reduction of cost and simplification of the structure.

When a culture container transporting set according to the present invention is used for culture state transportation, the vessel(s) of the culture container stores the contents (living cells or tissues being cultured and culture medium). That is, a unit comprising the culture container transporting set with the contents (living cells and tissues transporting unit) stored therein also falls within the scope of the present invention.

The invention claimed is:

1. A culture container transporting set comprising:
   a culture container having at least one vessel including a bottom wall and a tubular side wall raised from the bottom wall;
   a flexible cover that covers an upper end of the side wall of the vessel;
   a presser member that is hard and placed on the cover; and
   a holder that holds together a stacked assembly of the culture container, the cover and the presser member by applying pressure from top and bottom, wherein
   the cover comprises a projected portion that is accommodated inside the side wall and projects toward the bottom wall, the projected portion including an inner cylindrical portion and a bottom disposed at a lower end of the inner cylindrical portion, and
   the bottom of the projected portion comprises a thin portion that is smaller in thickness than remaining portions of the bottom, the thin portion having a form of a disk containing a center of the bottom in plan view, the thin portion being spaced apart from the inner cylindrical portion in plan view.

2. The culture container transporting set according to claim 1, wherein the cover includes a thick portion configured to come into intimate contact with the upper end of the side wall, the thick portion being greater in thickness than the thin portion, and the thin portion having gas permeability.

3. The culture container transporting set according to claim 2, wherein the thick portion has a re-sealing ability to seal a syringe needle puncture, and in an assembled state in which the culture container, the cover, and the presser member are stacked together, the thick portion is in intimate contact with a lower surface of the presser member.

4. The culture container transporting set according to claim 1, wherein the presser member is provided with a through-hole extending vertically at a location inside the side wall as viewed in the vertical direction.

5. The culture container transporting set according to claim 4, wherein the presser member is provided with a groove formed in an upper surface of the presser member to connect a peripheral edge of the presser member to the through-hole.

6. The culture container transporting set according to claim 1, wherein the holder includes a flat bottom plate, a top plate parallel to the bottom plate, and a pair of side plates each connected at opposite ends to the top plate and the bottom plate, the plates being connected to define a closed outline.

7. The culture container transporting set according to claim 1, wherein the holder includes: a bottom member having a flat bottom plate; a lid member detachably attached to the bottom member and having a top plate parallel to the bottom plate; and a fastener for fastening the bottom member and the lid member.

8. The culture container transporting set according to claim 1, further comprising an elastic sheet member having an ability to return to an original shape, and in an assembled state in which the culture container, the cover, and the presser member are stacked together, the elastic sheet member is stacked in contact with one of the culture container, the cover and the presser member.

9. The culture container transporting set according to claim 8, further comprising a side-surface cover that covers an entirety of a side surface of the bottom wall and a part of a side surface of the elastic sheet member.

10. The culture container transporting set according to claim 1, wherein the inner cylindrical portion is spaced apart from the side wall of the vessel.

11. The culture container transporting set according to claim 1, wherein the cover comprises an outer enclosure disposed outside the side wall of the vessel, and a distance between the outer enclosure and the inner cylindrical portion is greater than a thickness of the side wall of the vessel.

12. A living cell and tissue transporting unit comprising:
a culture container transporting set according to claim 1; and
a living cell or tissue and a culture medium that are stored in the vessel of the culture container transporting set.

* * * * *